US011399861B2

(12) United States Patent
Stulen et al.

(10) Patent No.: US 11,399,861 B2
(45) Date of Patent: **\*Aug. 2, 2022**

(54) FEATURES TO PROMOTE REMOVAL OF DEBRIS FROM WITHIN ULTRASONIC SURGICAL INSTRUMENT

(71) Applicant: Cilag GmbH International, Zug (CH)

(72) Inventors: Foster B. Stulen, Mason, OH (US); John A. Weed, III, Monroe, OH (US); Joseph Isosaki, Cincinnati, OH (US); Frederick L. Estera, Cincinnati, OH (US); Ryan M. Asher, Cincinnati, OH (US); Brian D. Black, Loveland, OH (US)

(73) Assignee: Cilag GmbH International Zug, Switzerland, Zug (CH)

( * ) Notice: Subject to any disclaimer, the term of this patent is extended or adjusted under 35 U.S.C. 154(b) by 173 days.

This patent is subject to a terminal disclaimer.

(21) Appl. No.: 16/549,809

(22) Filed: Aug. 23, 2019

(65) Prior Publication Data

US 2020/0069325 A1  Mar. 5, 2020

Related U.S. Application Data

(63) Continuation of application No. 15/643,585, filed on Jul. 7, 2017, now Pat. No. 10,478,211.

(51) Int. Cl.
*A61B 17/32* (2006.01)
*A61M 3/02* (2006.01)
(Continued)

(52) U.S. Cl.
CPC ......... *A61B 17/320092* (2013.01); *A61B 17/320016* (2013.01); *A61B 17/320068* (2013.01);
(Continued)

(58) Field of Classification Search
CPC .... A61B 17/320092; A61B 17/320068; A61B 17/320016; A61B 2017/320082;
(Continued)

(56) References Cited

U.S. PATENT DOCUMENTS 3,805,787 A * 4/1974 Banko ................. A61F 9/00745
604/22
3,812,855 A    5/1974 Banko
(Continued)

FOREIGN PATENT DOCUMENTS

EP         2581053      *  4/2013
EP         2581053 B1      9/2016
WO    WO 2004/110524 A2   12/2004

OTHER PUBLICATIONS

U.S. Pat. No. 10,478,211.
(Continued)

*Primary Examiner* — Theodore J Stigell
(74) *Attorney, Agent, or Firm* — Frost Brown Todd LLC

(57) ABSTRACT

An instrument includes an ultrasonic blade, a first fluid port, an irrigation member, a second fluid port, and a fluid communication assembly. The ultrasonic blade defines a distal opening. The ultrasonic blade is operable in a first mode to emulsify tissue that is distally positioned relative to the ultrasonic blade. The ultrasonic blade is further operable in a second mode to transect and seal tissue that is transversely positioned relative to the ultrasonic blade. The first fluid port is in communication with the distal opening of the ultrasonic blade. The irrigation member is positioned adjacent to the distal end of the ultrasonic blade. The second fluid port is in communication with the irrigation member. The fluid communication assembly is configured to couple the first fluid port with a fluid source, couple the first fluid port with a suction source, and couple the second fluid port with the fluid source.

19 Claims, 16 Drawing Sheets

(51) Int. Cl.
*A61M 1/00* (2006.01)
*A61B 17/00* (2006.01)
*A61B 17/28* (2006.01)
*A61B 18/00* (2006.01)
*A61B 17/29* (2006.01)

(52) U.S. Cl.
CPC ............ *A61M 1/0062* (2013.01); *A61M 1/74* (2021.05); *A61M 1/743* (2021.05); *A61M 1/774* (2021.05); *A61M 3/0283* (2013.01); *A61B 2017/00017* (2013.01); *A61B 2017/00022* (2013.01); *A61B 2017/00353* (2013.01); *A61B 2017/2825* (2013.01); *A61B 2017/2926* (2013.01); *A61B 2017/32007* (2017.08); *A61B 2017/32008* (2013.01); *A61B 2017/320069* (2017.08); *A61B 2017/320075* (2017.08); *A61B 2017/320082* (2017.08); *A61B 2017/320084* (2013.01); *A61B 2017/320093* (2017.08); *A61B 2017/320095* (2017.08); *A61B 2018/00589* (2013.01); *A61B 2018/00994* (2013.01); *A61B 2217/005* (2013.01); *A61B 2217/007* (2013.01); *A61B 2218/001* (2013.01); *A61B 2218/002* (2013.01); *A61B 2218/007* (2013.01); *A61M 3/022* (2014.02); *A61M 3/0208* (2014.02)

(58) Field of Classification Search
CPC ........... A61B 2017/2825; A61B 2017/320095; A61B 2017/32007; A61B 2017/320069; A61B 2017/320093; A61B 2017/320075; A61B 2017/00017; A61B 2017/00022; A61B 2017/00353; A61B 2017/2926; A61B 2017/32008; A61B 2017/320084; A61B 2018/00589; A61B 2018/00994; A61M 1/0031; A61M 3/0283; A61M 1/0035; A61M 1/0064; A61M 1/0062; A61M 3/0208; A61M 3/022
See application file for complete search history.

(56) References Cited

U.S. PATENT DOCUMENTS

| | | | |
|---|---|---|---|
| 4,368,734 A * | 1/1983 | Banko | A61F 9/00763 606/107 |
| 4,770,654 A | 9/1988 | Rogers et al. | |
| 4,935,005 A | 6/1990 | Haines | |
| 5,322,055 A * | 6/1994 | Davison | A61B 17/320068 601/2 |
| 5,725,495 A * | 3/1998 | Strukel | A61M 1/743 604/44 |
| 5,873,873 A | 2/1999 | Smith et al. | |
| 5,935,096 A * | 8/1999 | Barrett | A61F 9/00745 604/22 |
| 5,980,510 A | 11/1999 | Tsonton et al. | |
| 6,325,811 B1 | 12/2001 | Messerly | |
| 6,652,547 B2 | 11/2003 | Rabiner et al. | |
| 6,773,444 B2 | 8/2004 | Messerly | |
| 6,783,524 B2 | 8/2004 | Anderson et al. | |
| 8,057,408 B2 | 11/2011 | Cain et al. | |
| 8,152,825 B2 | 4/2012 | Madan et al. | |
| 8,461,744 B2 | 6/2013 | Wiener et al. | |
| 8,531,064 B2 | 9/2013 | Robertson et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 4/2015 | Miller et al. | |
| 9,095,367 B2 | 7/2015 | Olson et al. | |
| 9,381,058 B2 | 7/2016 | Houser et al. | |
| 9,393,037 B2 | 7/2016 | Olson et al. | |
| 10,178,999 B2 | 1/2019 | Komiya et al. | |
| 10,478,211 B2 * | 11/2019 | Stulen | A61B 17/320068 |
| 2006/0079874 A1 | 4/2006 | Faller et al. | |
| 2007/0083120 A1 | 4/2007 | Cain et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0237880 A1 * | 9/2011 | Hamel | A61B 1/015 600/104 |
| 2012/0116265 A1 | 5/2012 | Houser et al. | |
| 2013/0190623 A1 | 7/2013 | Bertolina et al. | |
| 2017/0007451 A1 * | 1/2017 | Depenbusch | A61M 1/85 |
| 2017/0105752 A1 * | 4/2017 | Boudreaux | A61B 17/320092 |
| 2017/0172699 A1 | 6/2017 | Otrembiak et al. | |

OTHER PUBLICATIONS

International Search Report and Written Opinion dated Jan. 7, 2019 for International Application No. PCT/US2018/040873, 20 pages.
U.S. Appl. No. 61/410,603, filed Nov. 5, 2010.
Indian Office Action dated Mar. 3, 2022, for Application No. 201917048609, 7 pages.

\* cited by examiner

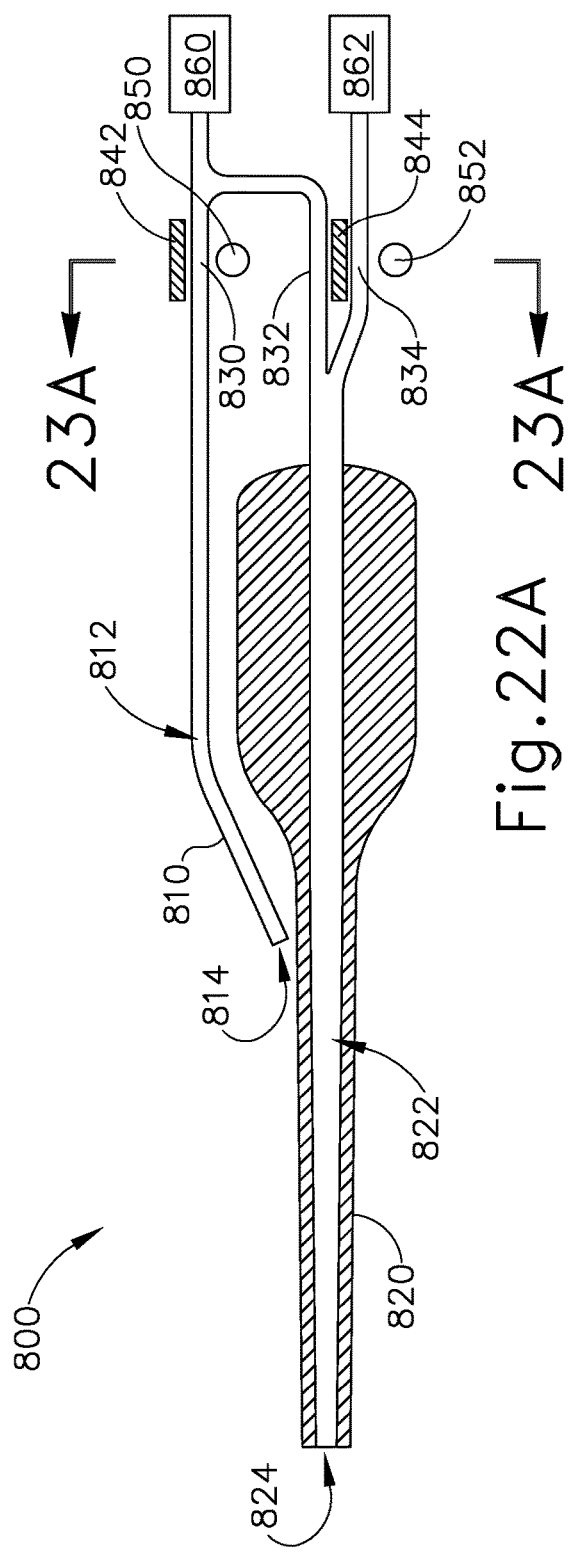
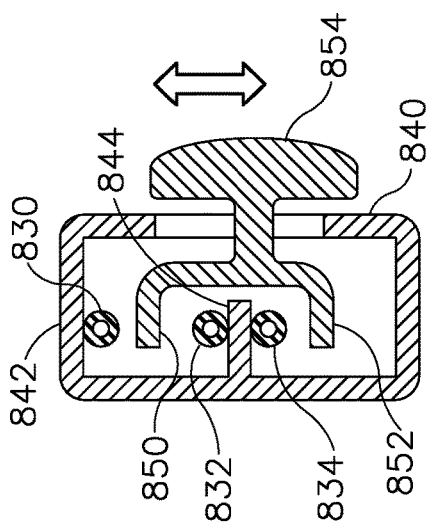
Fig.22A
Fig.23A

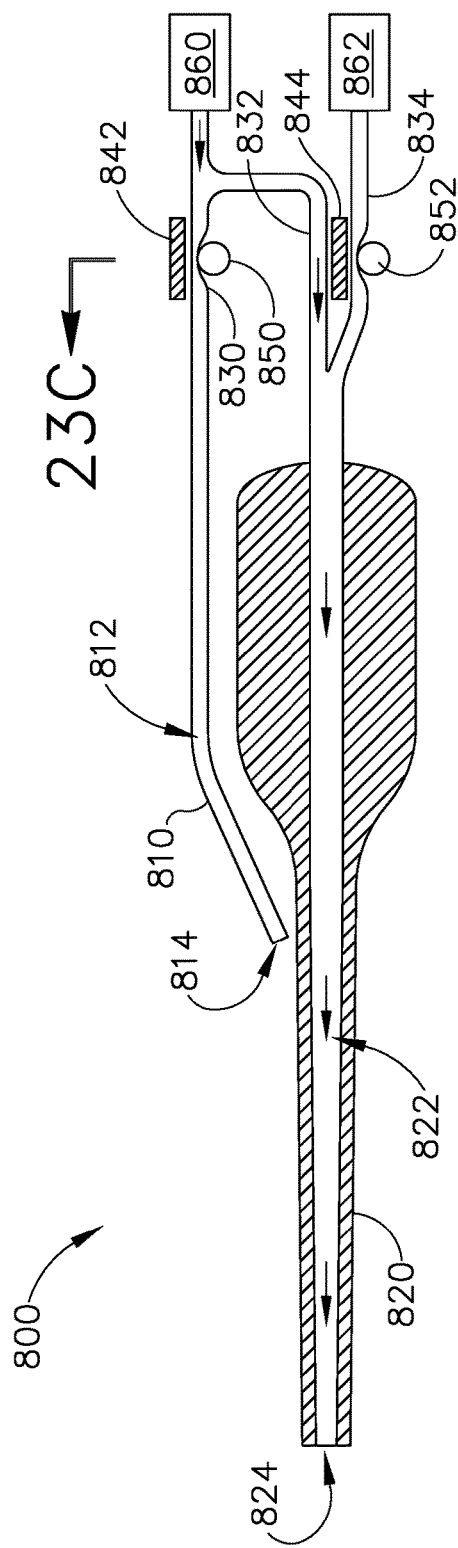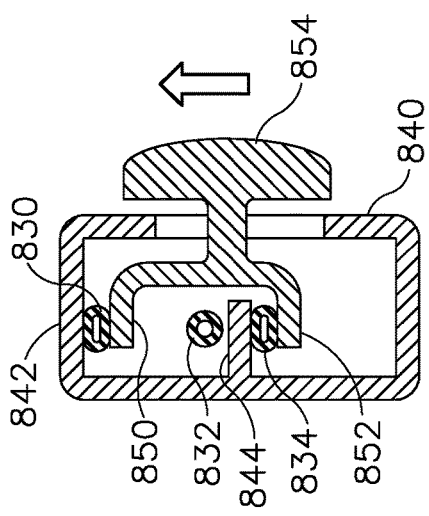
Fig.22C
Fig.23C

FEATURES TO PROMOTE REMOVAL OF DEBRIS FROM WITHIN ULTRASONIC SURGICAL INSTRUMENT

This application is a continuation of U.S. patent application Ser. No. 15/643,585 filed on Jul. 7, 2017, published as U.S. Pat. App. No. 2019/0008545 on Jan. 10, 2019, issued as U.S. Pat. No. 10,478,211 on Nov. 19, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jul. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jun. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

Some ultrasonic surgical instruments may include a clamp feature to press tissue against the ultrasonic blade of the end effector. Examples of such an arrangement (sometimes referred to as a clamp coagulator shears or an ultrasonic transector) is disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; and U.S. Pat. No. 6,325,811, entitled "Blades with Functional Balance Asymmetries for use with Ultrasonic Surgical Instruments," issued Dec. 4, 2001, the disclosure of which is incorporated by reference herein. Some versions of clamp coagulator shears utilize handles that are either of a pistol or scissors grips design. The scissor grip designs may have one thumb or finger grip that is immovable and fixed to the housing; and one movable thumb or finger grip. Some designs have scissor arms that extend from the grips, with one of the arms rotating around a fixed pivot or rotation point that is perpendicular to the longitudinal axis of the working element. The operator may thus squeeze a handgrip or other feature to drive a clamp arm, to thereby press the clamp pad toward the blade.

Some ultrasonic devices may be used to provide acoustic cavitation. When acoustic cavitation is used to break down soft tissue, the process may be referred to as "histotripsy." Examples of histotripsy techniques and associated technology are described in U.S. Pub. No. 2007/0083120, entitled "Pulsed Cavitational Ultrasound Therapy," published Apr. 12, 2007, now abandoned, the disclosure of which is incorporated by reference herein; U.S. Pub. No. 2013/0190623, entitled "Histotripsy Therapy Transducer," published Jul. 25, 2013, now abandoned, the disclosure of which is incorporated by reference herein; and U.S. Pat. No. 8,057,408, entitled "Pulsed Cavitational Ultrasound Therapy," issued Nov. 15, 2011, the disclosure of which is incorporated by reference herein. A somewhat similar procedure is known as lithotripsy, where shock waves are used to break up kidney stones. Such shock waves may be generated by an ultrasonic transducer.

Some ultrasonic devices may be used to provide tissue emulsification and ultrasonic shearing. Examples of such devices are described in U.S. Pub. No. 2017/0105752, entitled "Surgical Instrument Providing Ultrasonic Tissue Emulsification and Ultrasonic Shearing," published Apr. 20, 2017, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 22A depicts a cross-sectional side view of an exemplary alternative ultrasonic surgical instrument, with a valve assembly in a first state;

FIG. 22C depicts a cross-sectional side view of the instrument of FIG. 22A, with the valve assembly in a third state;

FIG. 23A depicts a cross-sectional view of the valve assembly of the instrument of FIG. 22A, taken along like 23A-23A of FIG. 22A, with the valve assembly in the first state;

FIG. 23C depicts a cross-sectional view of the valve assembly of the instrument of FIG. 22C, taken along like 23C-23C of FIG. 22C, with the valve assembly in the third state.

Figure 1:
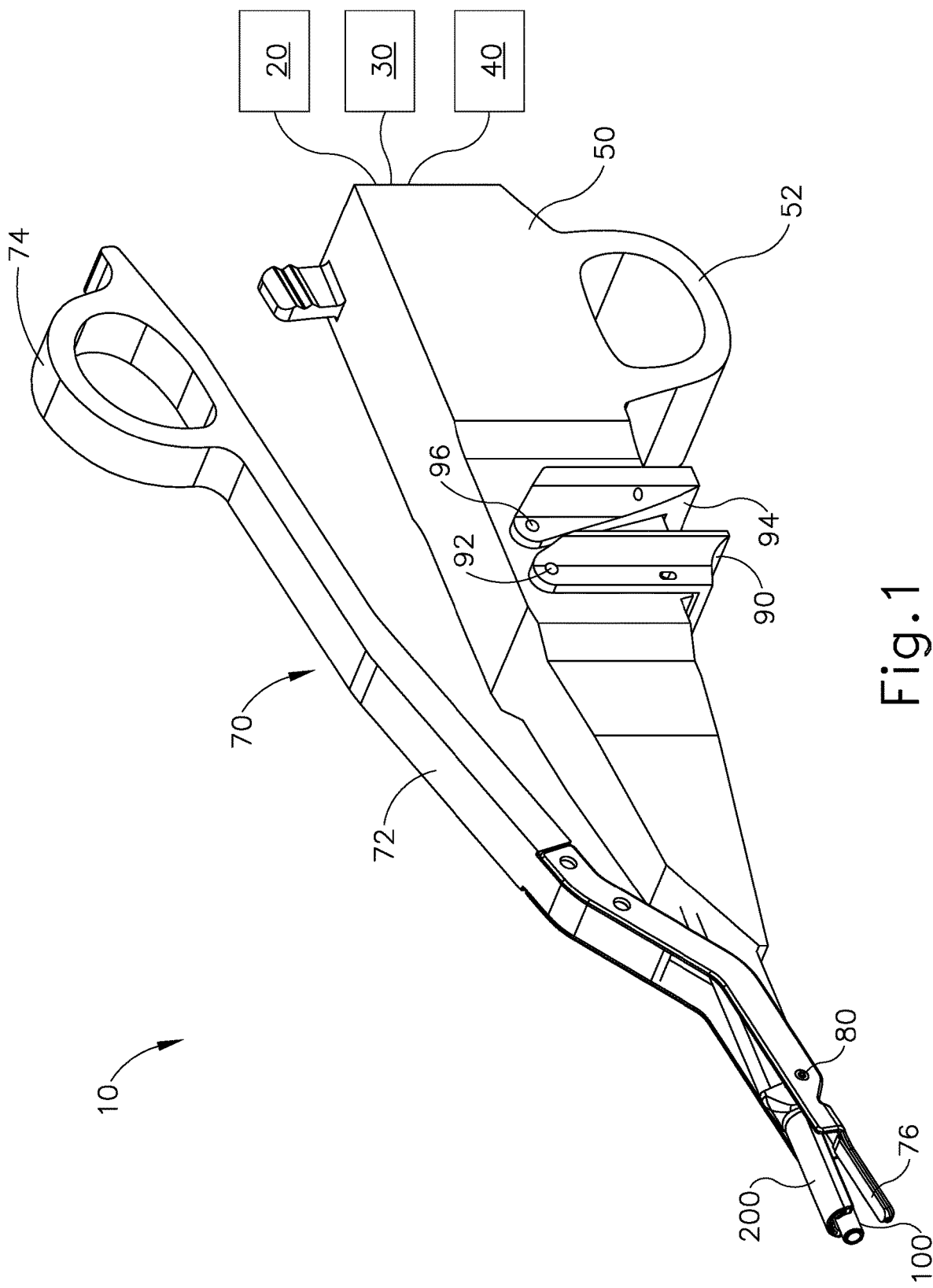
FIG. 1 depicts a perspective view of an exemplary ultrasonic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

In some surgical procedures, it may be desirable to operate an ultrasonic debriding instrument to dissect tissue by applying ultrasonic vibrational energy to the tissue. In the same surgical procedure, it may be desirable to operate an ultrasonic shears instrument to transect tissue by compressing the tissue against an ultrasonically activated element. In conventional instrumentation, this may require the use of two separate instruments. This is because, even though both types of instruments rely on activation of an ultrasonically vibrating element, the debriding instrument may act on tissue that is positioned distal to the ultrasonically vibrating element (e.g., along the longitudinal axis of the ultrasonically vibrating element); while the clamping transection instrument may act on tissue that is positioned transverse to the ultrasonically vibrating element (e.g., perpendicular to the longitudinal axis of the ultrasonically vibrating element). It may therefore be desirable to provide a single instrument that is operable to both provide dissection of tissue that is distal to an ultrasonically vibrating element and provide clamping transection in tissue that is positioned transverse to the ultrasonically vibrating element. Several merely illustrative examples of such an instrument are described in greater detail below.

It should be understood that the instruments described below may be used in a variety of clinical contexts. By way of example only, the instruments described below may be used to remove portions of a liver. In some such uses, the ultrasonically vibrating element may be used like a scalpel to dissect the parenchyma of the liver. This process may ultimately reveal one or more blood vessels and/or biliary ducts. In some such instances (e.g., where a vessel or duct having a diameter greater than approximately 1 mm is encountered), the scalpel-like mode of operation may not be an ideal mode to use for transecting and sealing such vessels and/or ducts. The operator may thus use a scalpel-like mode of operation to separate parenchymal tissue from vessels and biliary ducts in the liver, then transition use of the instrument to a clamping transection mode of operation in order to transect and seal the one or more blood vessels and/or biliary ducts. Various ways in which this may be accomplished will be described in greater detail below. It should be understood that integrating both modes of operation may reduce the number of instruments used in a surgical procedure, thereby simplifying the surgical procedure; and enabling the operator to keep the surgical field within their view the entire time that they are transitioning between modes of operation (whereas using two instruments may require the operator to avert their eyes from the surgical field, which may cause the operator to have difficulty finding the vessels/ducts that are to be transected). It should also be understood that this clinical context and method of operation is merely one of many possible contexts and methods in which the below described instruments may be used. Various other suitable contexts and methods in which the below described instruments may be used will be apparent to those of ordinary skill in the art in view of the teachings herein.

FIGS. 1-5 depict an exemplary instrument (10) that may be used to both provide an ultrasonic scalpel type of dissection in tissue that is distal to an ultrasonic blade (100) and provide clamping transection in tissue that is positioned transverse to ultrasonic blade (100). Instrument (10) of this example is coupled with a generator (20), a fluid source (30), and a suction source (40). Instrument (10) includes a handle assembly (50), a clamp arm assembly (70), and an irrigation flue (200) in addition to ultrasonic blade (100).

By way of example only, generator (20) may comprise the GEN04, GEN11, or GEN 300 sold by Ethicon Endo-Surgery, Inc. of Cincinnati, Ohio. In addition, or in the alternative, generator (20) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 4, 2015, the disclosure of which is incorporated by reference herein. Alternatively, any other suitable generator (20) may be used. As will be described in greater detail below, generator (20) is operable to provide power to instrument (10) to perform ultrasonic surgical procedures.

Fluid source (30) may contain saline and/or any other suitable kind(s) of fluid(s). It should also be understood that the fluid may comprise a high surface tension fluid with or without bubbles. In some versions, fluid source (30) comprises a passive reservoir that is positioned to provide fluid to instrument (10) via gravity feed. In some other versions, fluid source (30) includes a fluid pump and/or some other feature(s) that is/are operable to pressurize fluid for deliver to and through instrument (10). Various suitable forms that fluid source (30) may take, as well as various kinds of fluids that may be used, will be apparent to those of ordinary skill in the art in view of the teachings herein.

Suction source (40) may comprise any suitable source of suction. For instance, suction source (40) may comprise a conventional vacuum wall outlet that leads to a centralized vacuum system. Of course, one or more fluid reservoirs, filters, and/or other components may be interposed between instrument (10) and a conventional vacuum wall outlet. As another merely illustrative example, suction source (40) may comprise a vacuum pump that is situated locally with instrument (10). As yet another merely illustrative example, suction source (40) may be integrated into a single piece of capital equipment along with generator (20) and/or fluid source (30). Various other suitable forms that suction source (40) may take will be apparent to those of ordinary skill in the art in view of the teachings herein.

Handle assembly (50) of the present example includes an integral finger ring (52) through which an operator's finger may be inserted to facilitate gripping of handle assembly (50). Handle assembly (50) further includes a ratchet feature

(60) and a pair of triggers (90, 94). Each trigger (90, 94) is pivotably coupled with handle assembly (50) by a respective pin (92, 96). Ratchet feature (60) and triggers (90, 94) will be described in greater detail below. As shown ultrasonic blade (100) and irrigation flue (200) project distally from handle assembly (50).

Clamp arm assembly (70) comprises a shank (72), a thumb ring (74), and a clamp pad (76). Shank (72) is pivotably coupled with handle assembly (50) by a pin (80). Thumb ring (74) is configured to receive an operator's thumb to facilitate actuation of clamp arm assembly (70). It should therefore be understood that finger ring (52) and thumb ring (74) together enable an operator to grasp and manipulate instrument (10) using a scissor grip. Of course, such a configuration is merely optional. In some variations, instrument (10) is modified to provide a pistol grip with a pivoting trigger to control a clamp arm assembly. Various examples of such a configuration are shown and described in numerous references cited herein. As yet another merely illustrative example, some versions of instrument (10) may substitute handle assembly (50) and clamp arm assembly (70) with features that are coupled to a robotic surgical system that is configured to operate instrument (10) (e.g., via remote control, etc.).

Clamp arm assembly (70) is operable to pivot clamp pad (72) toward and away from ultrasonic blade (100). Clamp arm assembly (70) is thus operable to compress tissue between clamp pad (72) and ultrasonic blade (100). Those of ordinary skill in the art will recognize that, when ultrasonic blade (100) is activated to vibrate ultrasonically, the compression of tissue against ultrasonic blade (100) by clamp pad (72) may assist in further driving the ultrasonic vibrations of ultrasonic blade (100) through the tissue, thereby promoting transection and sealing of the tissue. By way of example only, clamp pad (72) may comprise polytetrafluoroethylene (PTFE) to reduce adhesion of tissue to clamp pad (72). Other suitable material(s) and/or configurations that may be incorporated into clamp pad (72) will be apparent to those of ordinary skill in the art in view of the teachings herein.

It should also be understood that ultrasonic blade (100) may include various materials to prevent or reduce adhesion of tissue to blade (100). By way of example only, the distal external surface of ultrasonic blade (100) in the region of clamp pad (72) may be coated with a polymer such as Xylan to further reduce the potential for sticking. In addition, the inner surface defining lumen (122) of ultrasonic blade (100) may be coated with a polymer to help lessen the occurrence of clogging. Various other suitable materials that may be incorporated into ultrasonic blade (100) will be apparent to those of ordinary skill in the art in view of the teachings herein.

A. Exemplary Ultrasonic Communication Features

Figure 2:
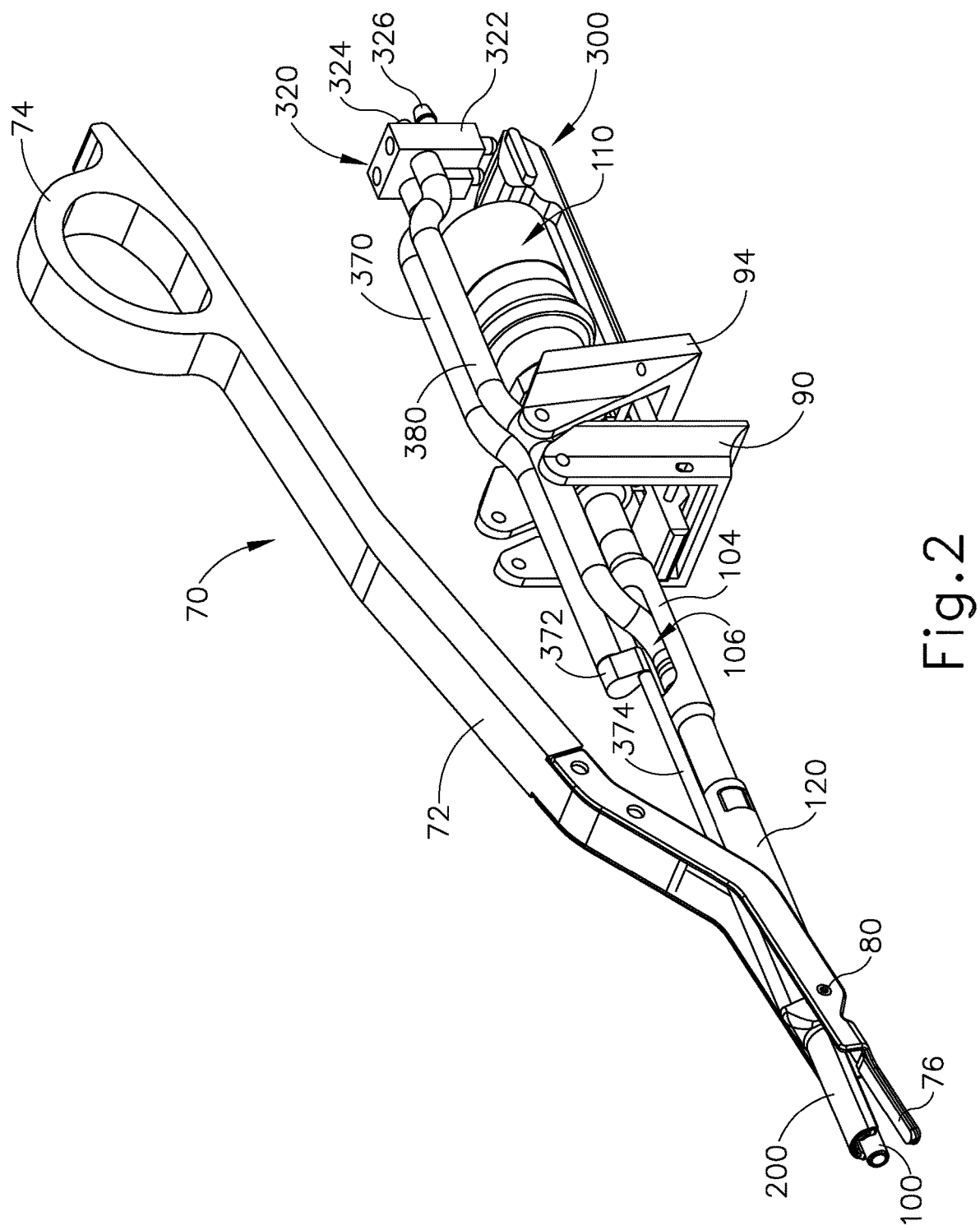
FIG. 2 depicts a perspective view of an ultrasonic surgical instrument of the system of FIG. 1, with a body of the instrument omitted for clarity.

As best seen in FIG. 2, an ultrasonic transducer assembly (110) is contained in handle assembly (50). Ultrasonic transducer assembly (110) receives electrical power from generator (20). Ultrasonic transducer assembly (110) includes a plurality of piezoelectric elements such that ultrasonic transducer assembly (110) is operable to convert electrical power from generator (20) into ultrasonic vibrational energy. Ultrasonic transducer assembly (110) of the present example includes two conductive rings (not shown) that are securely disposed within the body of ultrasonic transducer assembly (110) as is described in U.S. Pub. No. 2007/0106158, entitled "Medical Ultrasound System and Handpiece and Methods for Making and Tuning," published May 10, 2007, issued as U.S. Pat. No. 8,152,825 on Apr. 10, 2012, the disclosure of which is incorporated by reference herein. Other suitable forms that ultrasonic transducer assembly (110) may take will be apparent to those of ordinary skill in the art in view of the teachings herein.

Figure 4:
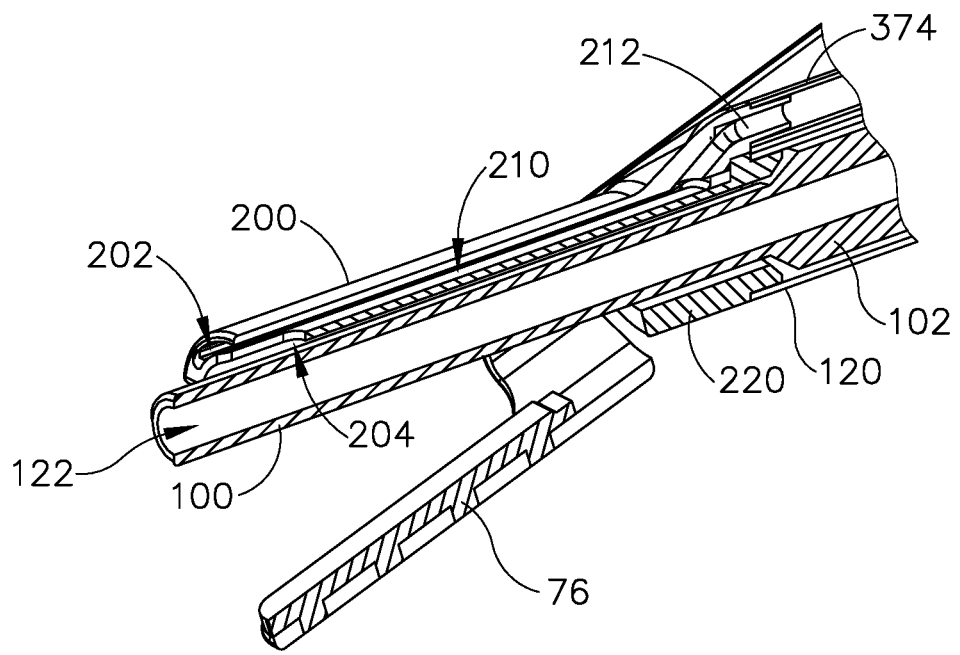
FIG. 4 depicts a cross-sectional perspective view of the end effector of FIG. 3, with the end effector in an open configuration.

As best seen in FIGS. 2 and 4, a proximal waveguide segment (104) is secured to the distal end of ultrasonic transducer assembly (110). A distal waveguide segment (102) is secured to the distal end of proximal waveguide segment (104). In particular, proximal waveguide segment (104) is secured to a coupling feature (124) (FIGS. 6-7) of distal waveguide segment (102). By way of example only, segments may be coupled together through welding, interference fitting, threaded coupling, and/or any other suitable form of coupling. Ultrasonic blade (100) is formed by the distal end of distal waveguide segment (102).

Figure 5:
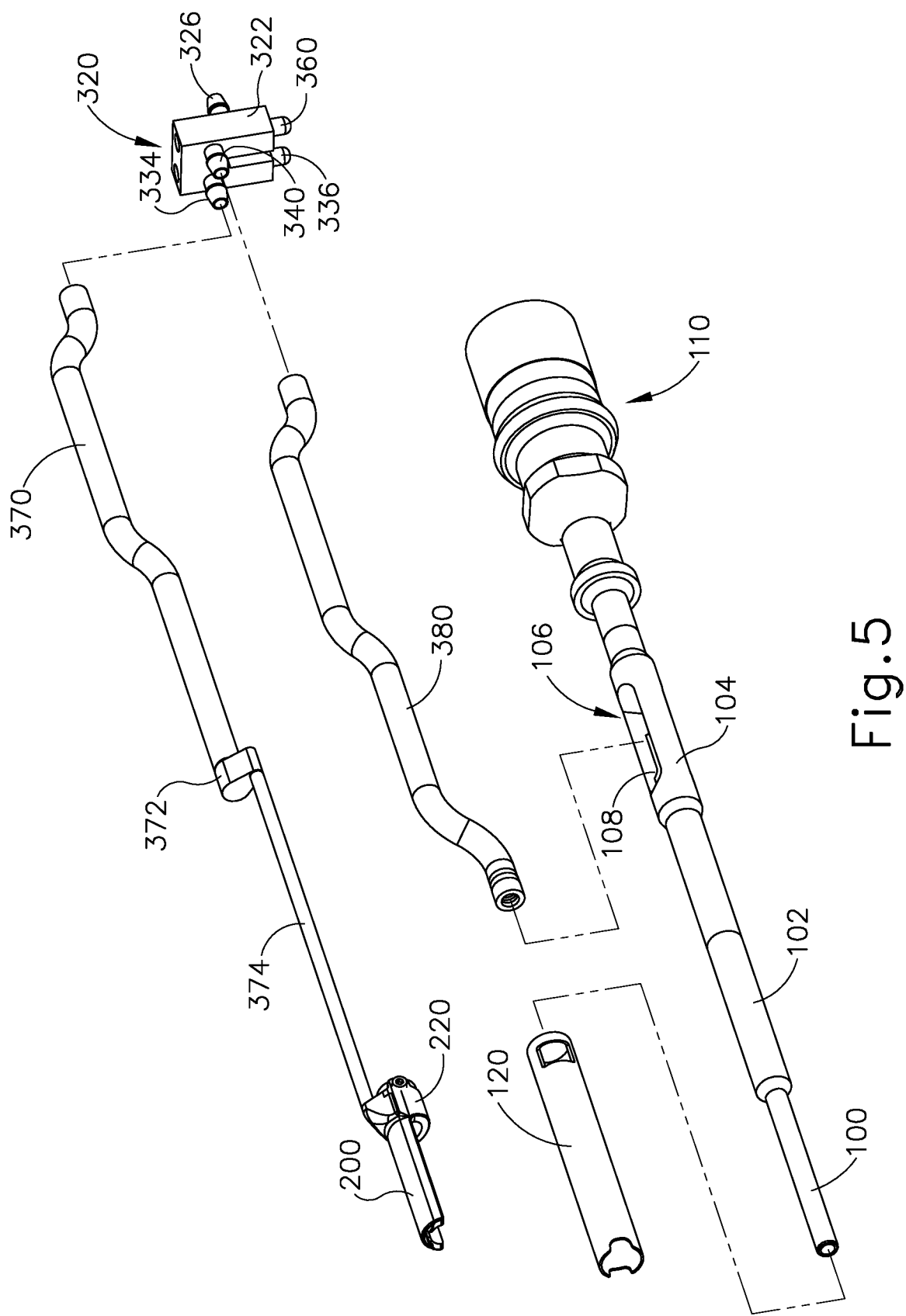
FIG. 5 depicts an exploded view of ultrasonic vibration transmission components, suction transmission components, and irrigating fluid transmission components of the instrument of FIG. 2.

In the present example, ultrasonic blade (100) is integral with distal waveguide segment (102), such that blade (100) and segment (102) are formed together as a single unit. In some versions, ultrasonic blade (100) may be connected to distal waveguide segment (102) by a threaded connection, a welded joint, and/or some other coupling feature(s). It should be understood that ultrasonic transducer assembly (110), segments (102, 104), and ultrasonic blade (100) together form an acoustic drivetrain, such that ultrasonic vibrations generated by ultrasonic transducer assembly (110) will be communicated along segments (102, 104) to blade (100). In some instances, coupling feature (124) is located at a longitudinal position corresponding to a node associated with ultrasonic vibrations communicated along segments (102, 104). Handle assembly (50) and clamp arm assembly (70) are configured to substantially isolate the operator from the vibrations of the acoustic assembly formed by ultrasonic transducer assembly (110), segments (102, 104), and ultrasonic blade (100). In addition, as shown in FIGS. 2 and 4-5, a distal sheath (120) is positioned about an otherwise exposed portion of distal waveguide segment (102), shielding distal waveguide segment (102) from inadvertent contact. Segments (102, 104) and ultrasonic blade (100) may be fabricated from a solid core shaft constructed out of a material or combination of materials that propagates ultrasonic energy efficiently, such as titanium alloy (i.e., Ti-6Al-4V), aluminum alloys, sapphire, ceramics (e.g., aluminum oxide, etc.), stainless steel, or any other acoustically compatible material or combination of materials.

Figure 6:
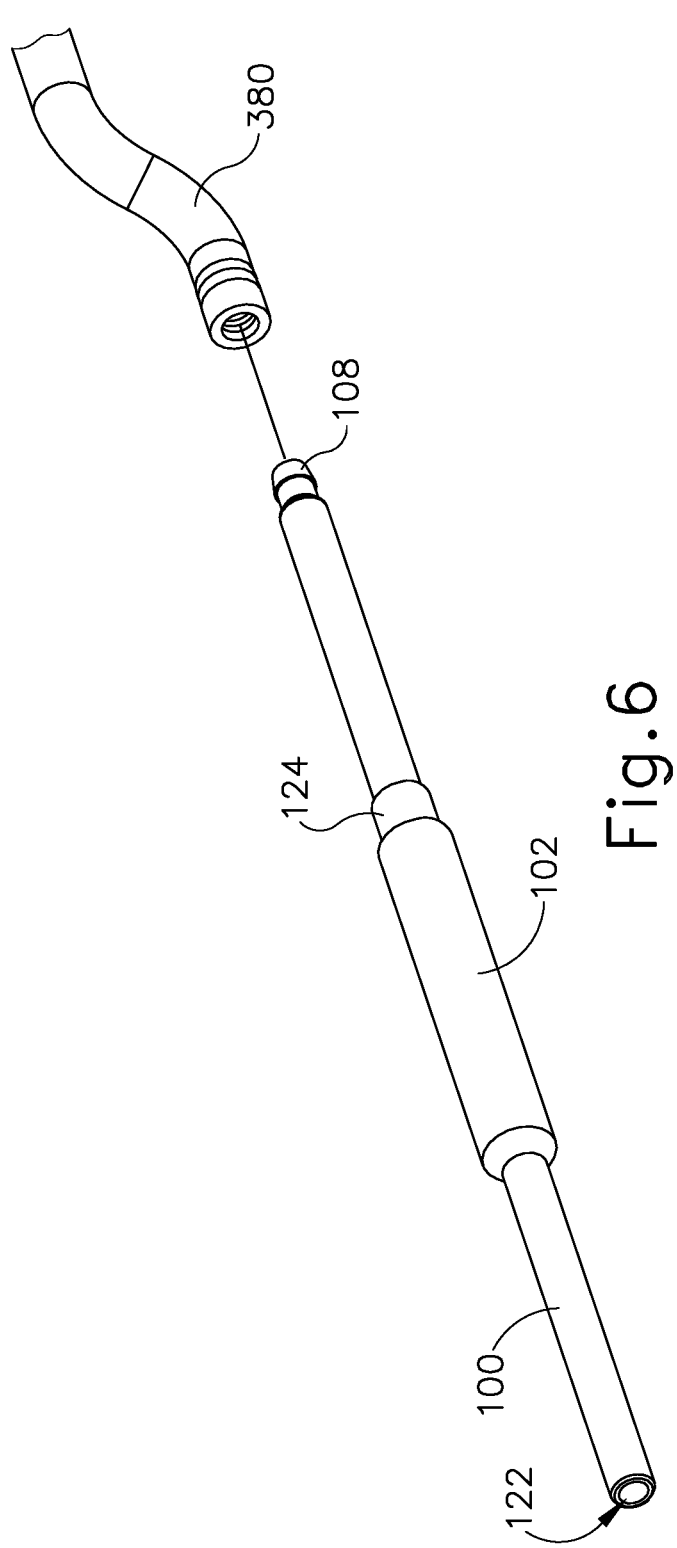
FIG. 6 depicts an exploded perspective view of a distal waveguide of the ultrasonic vibration transmission components of FIG. 5 separated from a suction tube of the suction transmission components of FIG. 5.
Figure 7:
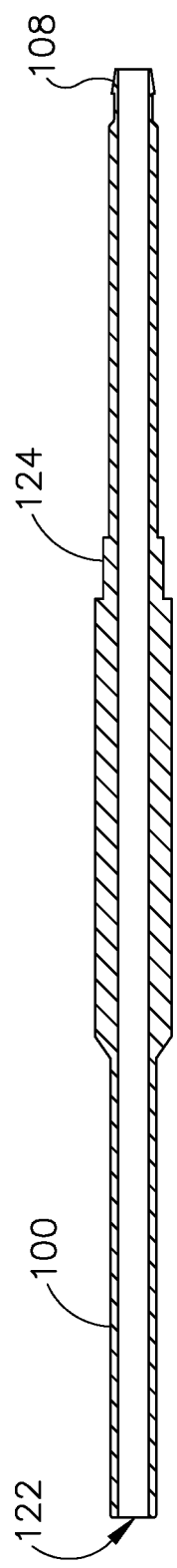
FIG. 7 depicts a cross-sectional side view of the distal waveguide of FIG. 6.

FIGS. 6-7 show ultrasonic blade (100) in greater detail. As shown, ultrasonic blade (100) of this example defines a lumen (122) such that ultrasonic blade (100) is hollow with open distal and proximal ends. The proximal end of ultrasonic blade (100) includes a barbed fitting (108). A suction tube (380) is coupled with barbed fitting (108) in a fluid-tight manner. It should therefore be understood that suction may be applied to the distal end of ultrasonic blade (100) via suction tube (380) and lumen (122). Suction tube (380) is further coupled with a valve assembly (320) as will be described in greater detail below. As best seen in FIGS. 2-5, proximal waveguide segment (104) defines a lateral channel (106) that is configured to accommodate the distal end of suction tube (380). In particular, suction tube (380) passes through lateral channel (106) to reach barbed fitting (108). Distal waveguide segment (102) thus receives suction from suction tube (380) despite the fact that segments (102, 104) are longitudinally aligned and coupled with each other. Other suitable ways in which suction may be provided through distal waveguide segment (102) will be apparent to those of ordinary skill in the art in view of the teachings herein.

When ultrasonic transducer assembly (110) of the present example is activated, these mechanical oscillations are transmitted through waveguide segments (102, 104) to reach ultrasonic blade (100), thereby providing oscillation of ultrasonic blade (100) at the resonant ultrasonic frequency. In the present example, the distal end of ultrasonic blade (100) is located at a position corresponding to an anti-node associated with resonant ultrasonic vibrations communicated through waveguide segments (102, 104). When ultrasonic transducer assembly (110) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. The distal tip of ultrasonic blade (100) may also vibrate in the y-axis at about 1 to about 10 percent of the motion in the x-axis. Of course, movement of the distal tip of ultrasonic blade (100) may alternatively have any other suitable characteristics. By way of example only, the distal tip of ultrasonic blade (100) may vibrate with more movement in the y-axis than in the x-axis. As another merely illustrative example, the distal tip of ultrasonic blade (100) may vibrate in the y-axis at up to about 50 percent of the motion in the x-axis. Other suitable vibrational characteristics will be apparent to those of ordinary skill in the art in view of the teachings herein. In the present example, the ultrasonic oscillation of ultrasonic blade (100) may simultaneously sever the tissue and denature the proteins in adjacent tissue cells, thereby providing a coagulative effect with relatively little thermal spread.

B. Exemplary Irrigation Flue

As shown in FIGS. 4-5, irrigation flue (200) of this example comprises an open distal end (202), a slot (204), a lumen (210), a fluid port (212), and a hub (220). Slot (204) extends longitudinally from open distal end (202). Open distal end (202), slot (204), and fluid port (212) are all in fluid communication with lumen (210). Fluid port (212) is configured to couple with a distal fluid tube (374), as shown in FIGS. 2 and 4-5. Fluid tube (374) is coupled with a fitting (372), which is further coupled with a proximal fluid tube (370). Proximal fluid tube (470) is further coupled with valve assembly (320) as will be described in greater detail below. It should be understood that the fluid from fluid source (30) may be communicated through open distal end (202) and slot (204) via valve assembly (320), proximal fluid tube (370), fitting (372), distal fluid tube (374), port (212), and lumen (210).

Hub (220) is secured to the distal end of sheath (120), such that the position of irrigation flue (200) is longitudinally and pivotably fixed relative to the position of ultrasonic blade (100) (other than the vibrational movement of ultrasonic blade (100) relative to irrigation flue (200)).

Figure 3:
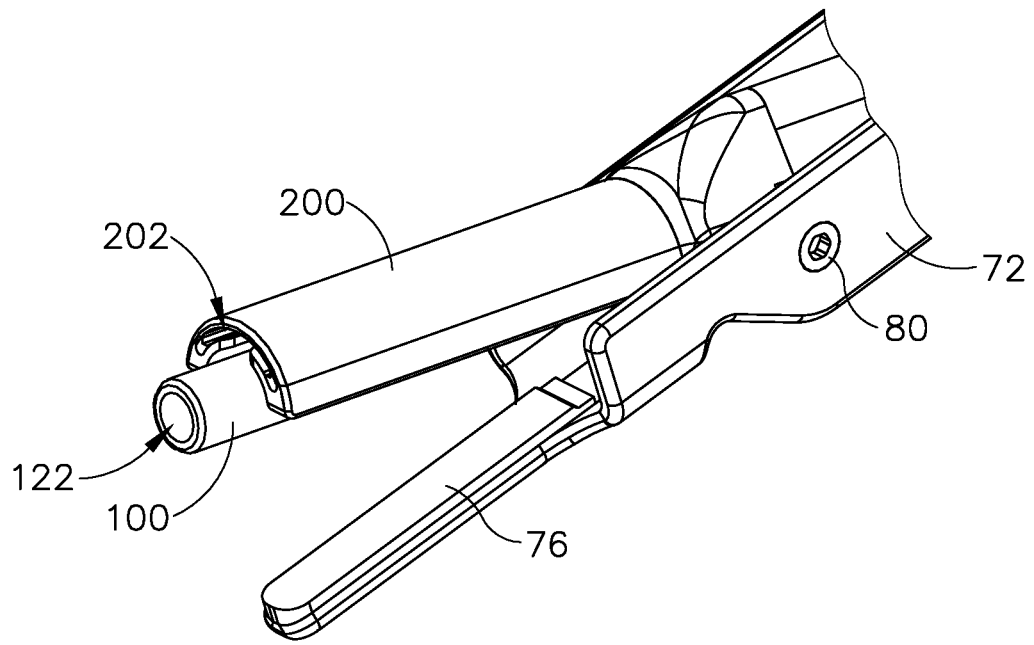
FIG. 3 depicts a perspective view of an end effector of the instrument of FIG. 2, with the end effector in an open configuration.

As best seen in FIGS. 3-4, irrigation flue (200) extends about a portion of the circumferential perimeter of ultrasonic blade (100), though irrigation flue (200) is sized and configured to maintain a gap between irrigation flue (200) and the distal end of ultrasonic blade (100). In the present example, irrigation flue (200) has a semi-circular cross-sectional profile with an angular extent of approximately 180°. This configuration and positioning prevents irrigation flue (200) from interfering with compression of tissue against ultrasonic blade (100) by clamp pad (76). Of course, this configuration is just one merely illustrative example. For instance, irrigation flue (200) may instead have a semi-circular cross-sectional profile with an angular extent that is less than or greater than approximately 180°. As another merely illustrative example, irrigation flue (200) may have a full circular cross-sectional profile extending a full 360° about ultrasonic blade (100), such that irrigation flue (200) is provided in the form of a tube. In some such versions, the gap between the inner diameter of irrigation flue (200) and the outer diameter of ultrasonic blade (100) serves as lumen (210). Thus, flue (200) may lack a lumen like lumen (210). Also in some such versions, a lateral cutout may be formed in the tube forming flue (200) in order to accommodate a full closure motion of clamp pad (72). Other suitable configurations for irrigation flue (200) will be apparent to those of ordinary skill in the art in view of the teachings herein.

C. Exemplary Valve Assembly

As shown in FIGS. 2 and 5, valve assembly (320) of this example includes a body (322), a fluid inlet port (324), a suction inlet port (326), a fluid outlet port (334), and a suction outlet port (336). Each port (324, 326, 334, 336) comprises a barbed fitting in this example, though it should be understood that this is just one merely illustrative example of form each port (324, 326, 334, 336) may take. Fluid inlet port (324) is coupled with fluid source (30) via conventional tubing and/or any other suitable kind of conduit. Suction inlet port (326) is coupled with suction source (40) via conventional tubing and/or any other suitable kind of conduit. As shown in FIGS. 2 and 5, fluid outlet port (324) is coupled with proximal fluid tube (370). As also shown in FIGS. 2 and 5, suction outlet port (324) is coupled with suction tube (380).

Valve assembly (320) further includes a fluid valve actuator (340) and a suction valve actuator (360). Valve actuators (340, 360) are slidably disposed in corresponding bores (354, 356) formed in body (322). Fluid valve actuator (340) is configured to selectively couple fluid outlet port (334) with fluid inlet port (324), based on the position of fluid valve actuator (340) in body (322). Suction valve actuator (360) is configured to selectively couple suction outlet port (336) with suction inlet port (326), based on the position of suction valve actuator (360) in body (322). Valve assembly (320) may be further configured and operable in accordance with at least some of the teachings of U.S. Pub. No. 2017/0105752, entitled "Surgical Instrument Providing Ultrasonic Tissue Emulsification and Ultrasonic Shearing," published Apr. 20, 2017, the disclosure of which is incorporated by reference herein.

In the present example, actuators (340, 360) travel upwardly simultaneously together and downwardly simultaneously together. Thus, whenever suction is being provided to ultrasonic blade (100), fluid is being provided to irrigation flue (200) and vice-versa. Similarly, whenever suction is not being provided to ultrasonic blade (100), fluid is not being provided to irrigation flue (200) and vice-versa. In some other versions, actuators (340, 360) may be actuated independently relative to each other. In some such versions, suction may be provided through blade (100) without fluid being provided through irrigation flue (200). In addition, or in the alternative, fluid may be provided through irrigation flue (200) without suction being provided through blade (100). Various suitable ways in which such functionality may be incorporated into instrument (10) will be apparent to those of ordinary skill in the art in view of the teachings herein.

II. Exemplary Features to Promote Removal of Debris from within Ultrasonic Surgical Instrument When tissue is emulsified by ultrasonic blade (100), the process may create loose fragments of tissue. These fragments of tissue may be drawn into ultrasonic blade (100) by suction provided through lumen (122). During the course of use of instrument (10) in a given surgical procedure, such tissue fragments, perhaps in combination with coagulated blood and/or other debris, may eventually build up within lumen (122). Such a build-up within lumen (122) may restrict the flow through lumen (122). Such restriction may eventually result in clogging of lumen (122). It may therefore be desirable to provide features and/or operational techniques that reduce the likelihood of tissue, etc. building up in lumen (122). Examples of such features and techniques are described in greater detail below.

Figure 8A:
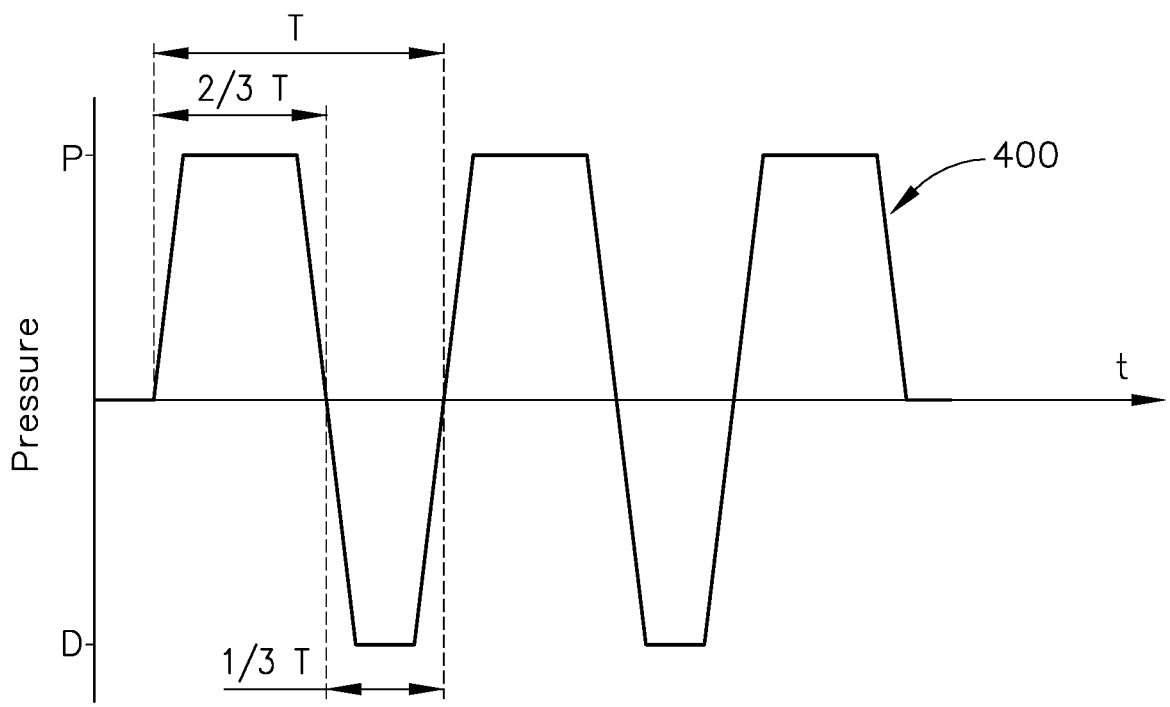
FIG. 8A depicts a graph showing an exemplary algorithm for alternating between proximally oriented pressure and distally oriented pressure during operation of the instrument of FIG. 2.

A. Exemplary Use of Reversible Fluid Flow to Prevent Clogging of Ultrasonic Blade Lumen One exemplary technique that may be employed to prevent the buildup of debris in lumen (122) includes providing a combination of negative, proximally-oriented fluid pressure and positive, distally-oriented fluid pressure in lumen (122). For instance, FIG. 8A shows a plot (400) of pressure over time where a duty cycle starts with negative, proximally-oriented fluid pressure (represented by "P" on the pressure axis) through lumen (122), then transitions to a positive, distally-oriented fluid pressure (represented by "D" on the pressure axis) through lumen, alternating back and forth between these two pressure orientations. This duty cycle may be carried out during normal operation of instrument (10).

Figure 8B:
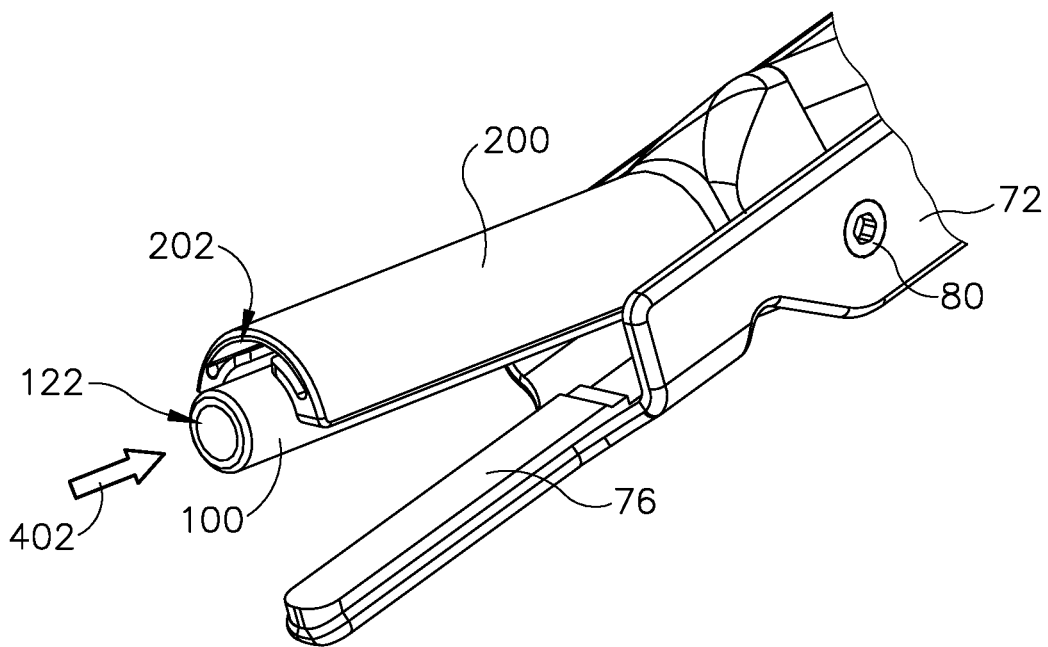
FIG. 8B depicts a perspective view of the end effector of FIG. 3 during performance of a portion of the algorithm of FIG. 8A.

In this example, the duration of the negative, proximally-oriented fluid pressure exceeds the duration of the positive, distally-oriented fluid pressure in each cycle. In particular, where each cycle has a total duration of time (T), the duration of the negative, proximally-oriented fluid pressure is two thirds of that time (T) and the duration of the positive, distally-oriented fluid pressure is one third of that time (T). Alternatively, other suitable relationships may be used. In the present example, the relationship provides a net negative, proximally-oriented fluid pressure, as represented by arrow (402) in FIG. 8B. The alternating pressure direction provided through duty cycle may provide a stirring action within lumen (122) to prevent debris from adhering to the sidewall of lumen (122), thereby preventing the debris from clogging or otherwise restricting flow through lumen (122).

Figure 9A:
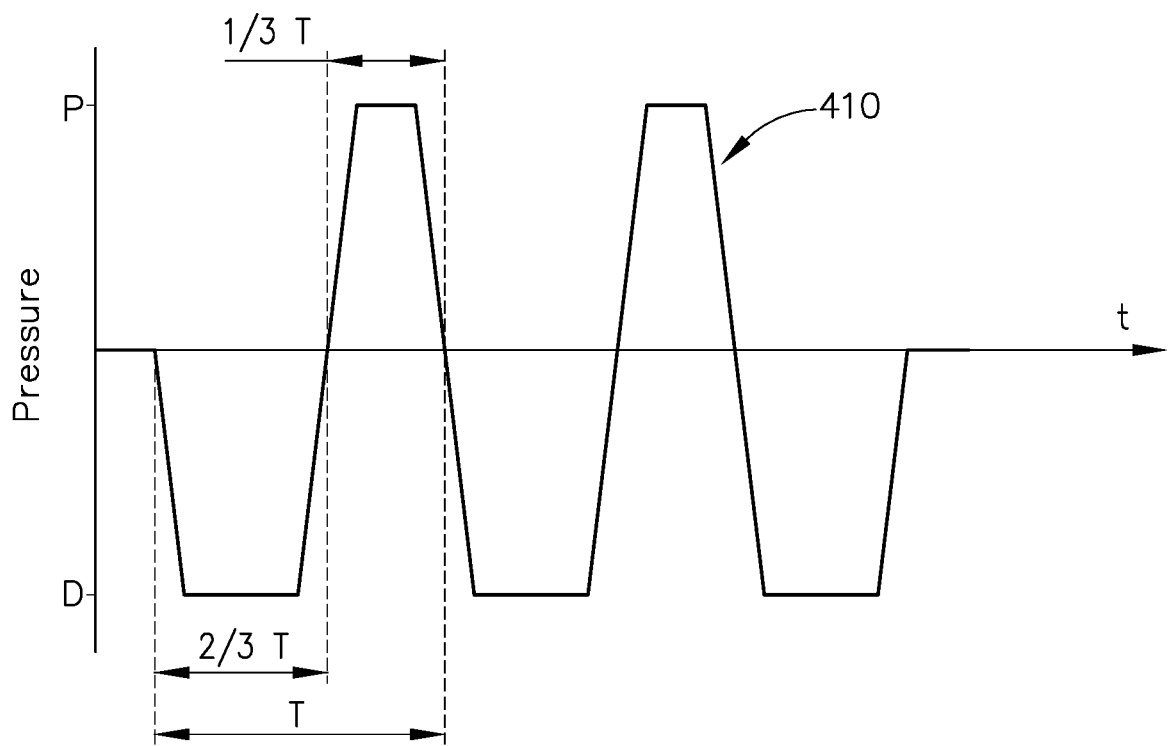
FIG. 9A depicts a graph showing an exemplary algorithm for alternating between proximally oriented pressure and distally oriented pressure during operation of the instrument of FIG. 2.
Figure 9B:
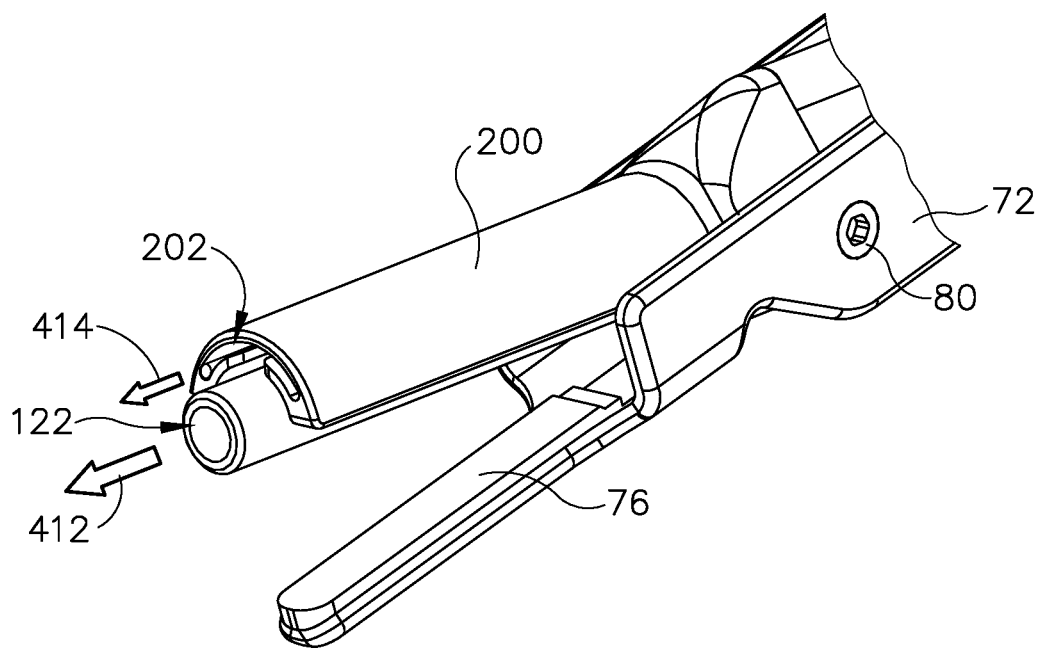
FIG. 9B depicts a perspective view of the end effector of FIG. 3 during performance of a portion of the algorithm of FIG. 9A.

In the event that a clog or other restriction occurs in lumen (122), the duty cycle may be changed to provide a net positive, distally-oriented fluid pressure, as represented by arrows (412, 414) in FIG. 9B. The duty cycle for such operation is shown by plot (410) in FIG. 9A. In this example, the duration of the positive, distally-oriented fluid pressure exceeds the duration of the negative, proximally-oriented fluid pressure in each cycle. In particular, where each cycle has a total duration of time (T), the duration of the positive, distally-oriented fluid pressure is two thirds of that time (T) and the duration of the negative, proximally-oriented fluid pressure is one third of that time (T). Alternatively, other suitable relationships may be used. The net positive, distally-oriented fluid pressure, as represented by arrows (412, 414) in FIG. 9B, may provide a flushing effect that dislodges the built-up debris in lumen (122).

Figure 10:
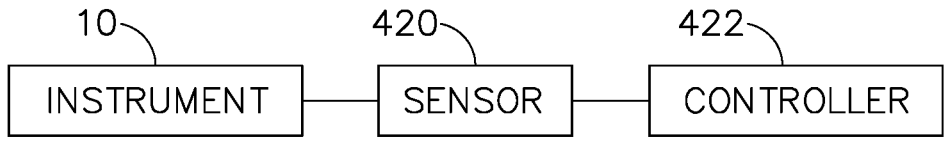
FIG. 10 depicts a schematic view showing a combination of the instrument of FIG. 2 with a sensor and a controller.

FIG. 10 shows an exemplary combination of features that may be used to automate a transition between the duty cycle shown in FIG. 8A and the duty cycle shown in FIG. 9A. In particular, FIG. 10 shows a sensor (420) and a controller (422) coupled with instrument (10). Sensor (420) is operable to detect a clog or other restriction in lumen (122). Various suitable forms that sensor (420) may take will be apparent to those of ordinary skill in the art in view of the teachings herein. Controller (422) is operable to process data from sensor (420) and execute an algorithm to toggle between the duty cycle shown in FIG. 8A and the duty cycle shown in FIG. 9A. Various suitable forms that controller (422) may take will be apparent to those of ordinary skill in the art in view of the teachings herein. While sensor (420) and controller (422) are depicted as being separate from instrument (10), sensor (420) and/or controller (422) may in fact be integrated into instrument (10).

Figure 11:
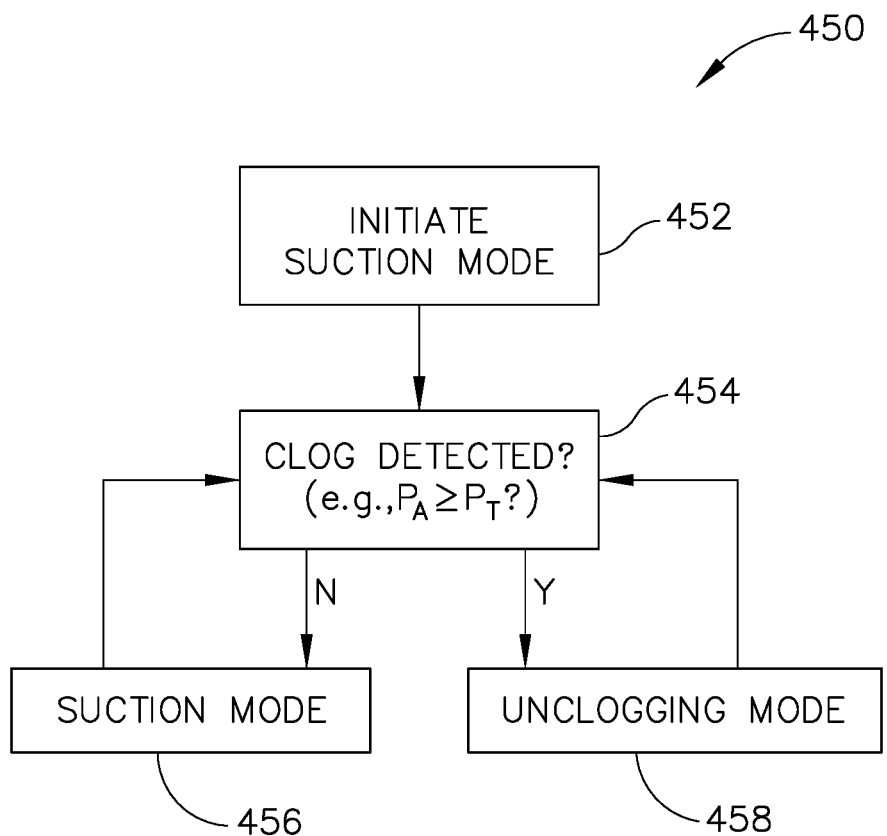
FIG. 11 depicts a flow chart showing an exemplary method of operation that may be carried out using the combination of FIG. 10.

FIG. 11 shows a method (450) that may be carried out using the combination of instrument (10), sensor (420), and controller (422). The method (450) is carried out while ultrasonic blade (100) is being used to emulsify tissue. The method (450) starts with initiation of the suction mode (block 452), which corresponds with the duty cycle shown in the plot (400) of FIG. 8A. While instrument (10) is operating in this suction mode, sensor (420) monitors the status of lumen (122) (block 454) to determine whether a clog or other restriction is present. If sensor (420) determines that a clog or other restriction is not present, instrument (10) continues to operate in suction mode (block 456) and sensor (420) continues to monitor the status of lumen (122) (block 454). If sensor (420) detects a clog or other restriction, controller (422) toggles instrument (10) to unclogging mode (block 456), which corresponds with the duty cycle shown in the plot (410) of FIG. 9A. While instrument (10) is operating in this unclogging mode, sensor (420) continues to monitor the status of lumen (122) (block 454) to determine whether the clog or other restriction has been cleared. Once the clog or other restriction is cleared, controller (422) toggles instrument (10) back to the suction mode (block 456).

Various kinds of components may be used to provide a duty cycle that alternates between a positive, distally-oriented pressure through lumen (122) and a negative, proximally-oriented pressure through lumen (122). By way of example only, such components may comprise a combination of a source of fluid (e.g., saline) at a positive pressure (e.g., fluid source (30)), a source of negative pressure (e.g., suction source (40)), and a valve coupled with lumen (122) to switch between these two sources. As another example, a reversible peristaltic pump or other kind of reversible pump may be used to alternate the direction of fluid flow through lumen (122). Other suitable components and techniques that may be used to provide a duty cycle that alternates between a positive, distally-oriented pressure through lumen (122) and a negative, proximally-oriented pressure through lumen (122) will be apparent to those of ordinary skill in the art in view of the teachings herein.

Figure 12:
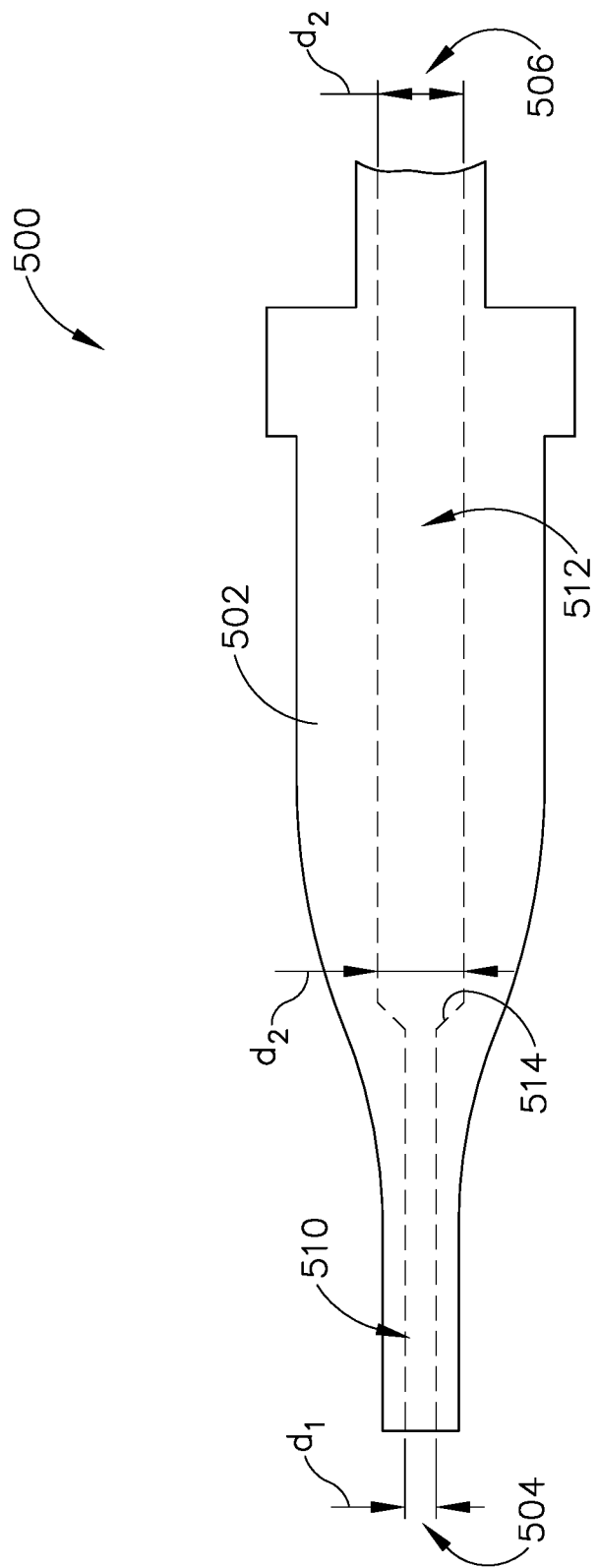
FIG. 12 depicts a cross-sectional side view of an exemplary alternative ultrasonic blade that may be incorporated into the instrument of FIG. 2.

B. Exemplary Alternative Ultrasonic Blade with Lumen Having Varying Inner Diameter FIG. 12 shows an exemplary alternative ultrasonic blade (500) that may be incorporated into instrument (10) in place of ultrasonic blade (100). Blade (500) of this example includes a body (502) defining a distal lumen (510) and a proximal lumen (512). Lumens (510, 512) are coaxially aligned with each other and are in fluid communication with each other. Lumen (510) distally terminates in a distal opening (504). Lumen (512) proximally terminates in a proximal opening (506). A tapered internal sidewall (514) provides a tapered transition between lumens (510, 512). In some versions, suction is provided through lumens (510, 512) as described above. In some other versions, a combination of suction and positive, distally-oriented fluid pressure is provided through lumens (510, 512), as also described above.

Lumen (510) has a first inner diameter ($d_1$) while lumen (512) has a second inner diameter ($d_2$). The first inner diameter ($d_1$) is constant along the length of lumen (510); while the second inner diameter ($d_2$) is constant along the length of lumen (512). Second inner diameter ($d_2$) is larger than first inner diameter ($d_1$). The relatively larger size of second inner diameter ($d_2$) may reduce the likelihood of debris building up within lumen (512). It may therefore be desirable to extend lumen (512) distally as far as possible without adversely impacting the ultrasonic emulsifying capabilities of ultrasonic blade (500). By providing a tapered transition from lumen (510) to lumen (512), tapered internal sidewall (514) may reduce the risk of debris building up at the transition from lumen (510) to lumen (512).

While ultrasonic blade (500) has two different inner diameters ($d_1$, $d_2$) in this example, some other versions may have more than two different inner diameters, with the inner diameters progressively increasing in size along the proximal direction.

C. Exemplary Ultrasonic Surgical Instrument with Lumen Access Hatch

Figure 13A:
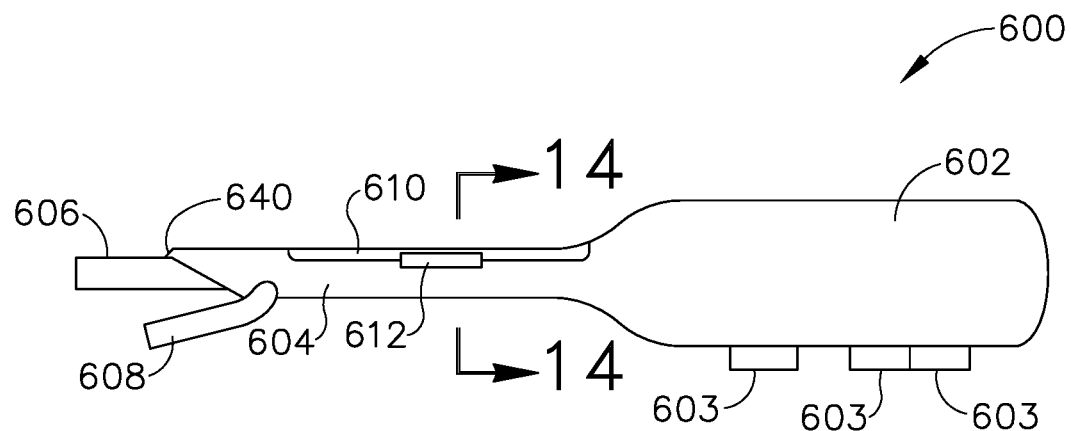
FIG. 13A depicts a side elevational view of an exemplary alternative ultrasonic surgical instrument, with an access hatch in a closed position.
Figure 13B:
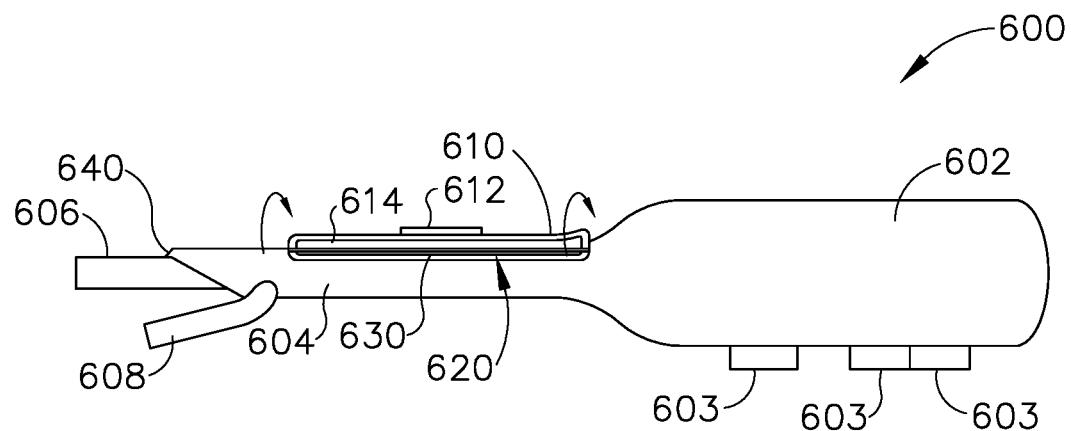
FIG. 13B depicts a side elevational view of the instrument of FIG. 13A, with the access hatch in an open position.

In addition to, or as an alternative to, providing varying fluid flow and/or a varying fluid flow path within instrument (10), it may be desirable to provide features that enable the operator to directly access and remove debris from lumen (122) of ultrasonic blade (100). FIGS. 13A-13B show an exemplary alternative ultrasonic surgical instrument (600) that provides such capabilities. Except as otherwise described below, instrument (600) of this example is configured and operable just like instrument (10) described above. Instrument (600) of this example comprises a body (602), a shaft, (604), an ultrasonic blade (606), a clamp arm (608), and an irrigation flue (640). A plurality of buttons (603) are used to provide operation of instrument (600), though any other suitable kinds of user input features may be used. Ultrasonic blade (606) is operable to vibrate at ultrasonic frequencies; and to provide suction to draw away fluid (e.g., saline, blood, etc.) and debris (e.g., tissue fragments, etc.). Clamp arm (608) is pivotable toward and away from ultrasonic blade (606) to assist in transection and sealing of tissue as described above.

Figure 14:
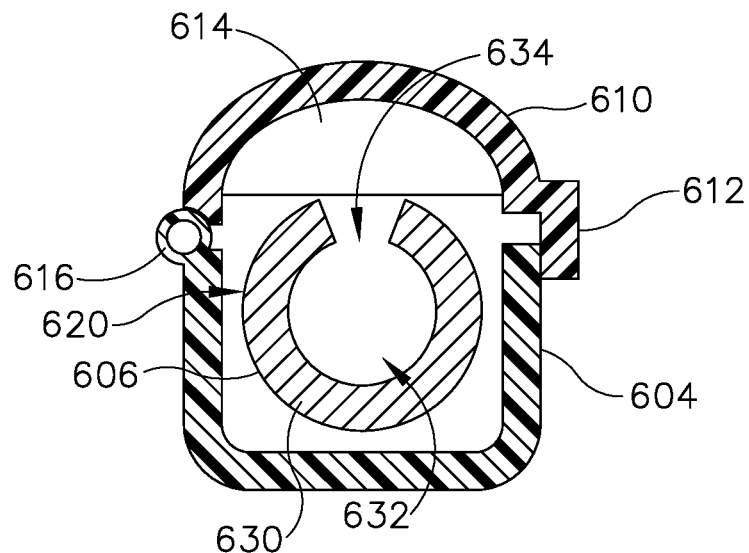
FIG. 14 depicts a cross-sectional view of the instrument of FIG. 13A, taken along line 14-14 of FIG. 13A.
Figure 15:
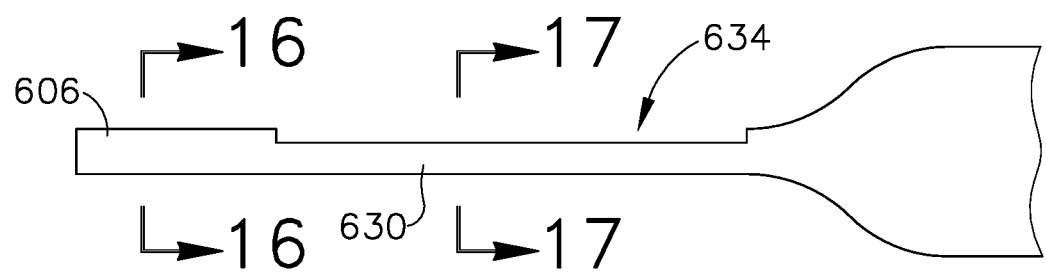
FIG. 15 depicts a side elevational view of a distal portion of an ultrasonic blade of the instrument of FIG. 13A.
Figure 16:
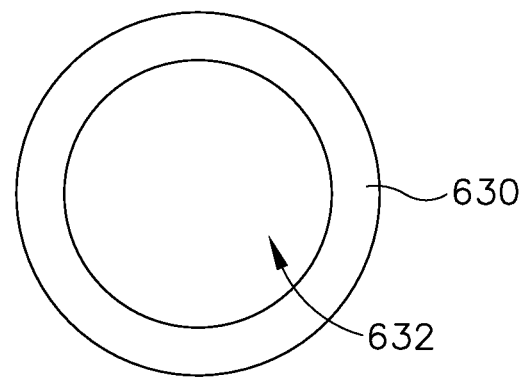
FIG. 16 depicts a cross-sectional view of the ultrasonic blade of FIG. 15, taken along line 16-16 of FIG. 15.
Figure 17:
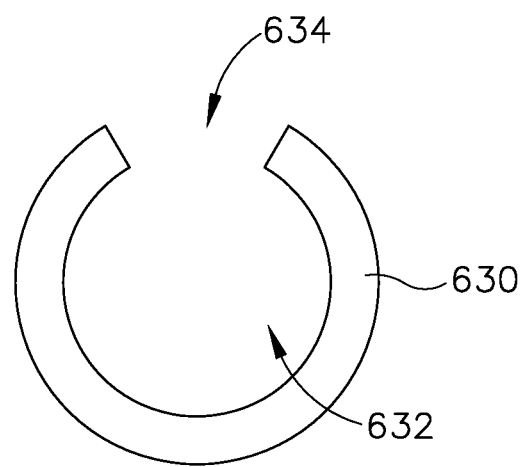
FIG. 17 depicts a cross-sectional view of the ultrasonic blade of FIG. 15, taken along line 17-17 of FIG. 15.

Instrument (600) of the present example differs from instrument (10) in that instrument (600) of the present example includes a hatch (610) that selectively opens and closes a lateral opening (620) of shaft (604). Hatch (610) is configured to transition between a closed position (FIG. 13A) and an open position (FIG. 13B). As shown in FIG. 14, a hinge (616) provides the pivotal movement of hatch (610), while a latch (612) selectively retains hatch (610) in the closed position. As shown in FIGS. 15-17, ultrasonic blade (606) includes a body (630) that defines a lumen (632) and a lateral notch (634). Body (630) has a circular cross-sectional profile in this example. Lateral notch (634) is in communication with lumen (632). Lateral notch (634) is located proximal to the distal end of ultrasonic blade (606) and extends longitudinally along only a portion of the length of body (630).

As shown in FIGS. 13B and 14, the underside of hatch (610) includes a gasket (614). Gasket (614) may comprise an elastomeric material. As shown in FIG. 14, gasket (614) is configured to engage body (630) and effectively seal lateral notch (634) when hatch (610) is in the closed position. Gasket (614) extends along the full length of lateral notch (634). In the present example, gasket (614) is longer than lateral notch (634), such that the distal end of gasket (614) is distal to the distal end of lateral notch (634); and the proximal end of gasket (614) is proximal to the proximal end of lateral notch (634).

During normal operation of instrument (600) in a surgical procedure, hatch (610) remains in the closed position. In the event that lumen (632) of ultrasonic blade (606) becomes clogged, the operator may open hatch (610) to access lateral notch (634). The operator may then insert a wire, brush, or other cleaning instrument through lateral notch (634) to clear debris from lumen (632). During this cleaning, suction may be provided through lumen (632). Alternatively, saline or some other fluid may be communicated through lumen (632) at a positive pressure as the operator cleans lumen (632) via lateral notch (634). Alternatively, a duty cycle such as the one shown in FIG. 8A or the one shown in FIG. 9B may be provided through lumen (632) as the operator cleans lumen (632) via lateral notch (634). Alternatively, no fluid or suction may be provided through lumen (632) as the operator cleans lumen (632) via lateral notch (634).

D. Exemplary Alternative Cross-Sectional Profiles for Ultrasonic Blade

Figure 18:
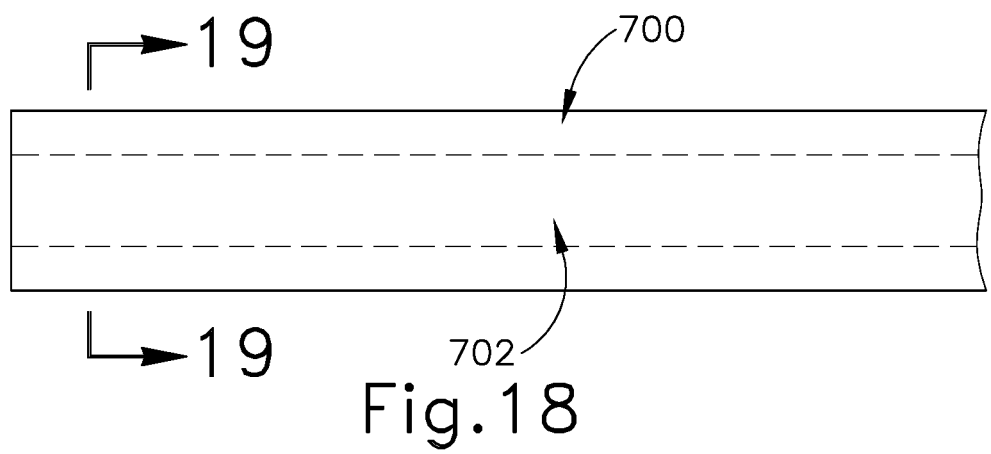
FIG. 18 depicts a side elevational view of a distal portion of another exemplary alternative ultrasonic blade.
Figure 19:
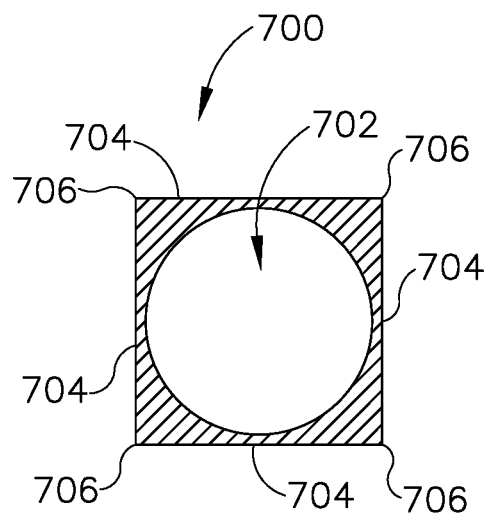
FIG. 19 depicts a cross-sectional view of the ultrasonic blade of FIG. 18, taken along line 19-19 of FIG. 18.

In addition to, or as an alternative to, the features and techniques described above, a variation of instrument (10) may include features that provide enhanced fragmentation of tissue. By providing enhanced fragmentation of tissue, the tissue particles may be finer and thereby less likely to clog lumen (122) of ultrasonic blade (100). FIGS. 18-19 show an exemplary alternative ultrasonic blade (700) that may provide such enhanced tissue fragmentation. Ultrasonic blade (700) may be incorporated into instrument (10) in place of ultrasonic blade (100). Ultrasonic blade (700) of this example defines a lumen (702) and includes four flat faces (704) that meet at sharp corners (706). Ultrasonic blade (700) thus has a square outer cross-sectional profile. By providing corners (706), ultrasonic blade (700) may have a greater mass than an ultrasonic blade (100) that has a circular cross-sectional profile. This added mass may provide enhanced tissue fragmentation (e.g., by increasing the speed of tissue fragmentation).

By way of example only, ultrasonic blade (100) may have an outer diameter of 0.100 inches with an inner diameter of 0.080 inches. Ultrasonic blade (700) may have flat faces (704) with widths of 0.100 inches and an inner diameter of 0.080 inches. Despite the similarities between the values of these size parameters, ultrasonic blade (700) of this example would have a cross-sectional area that is 76% larger than the cross-sectional area of ultrasonic blade (100) of this example. This larger cross-sectional area would provide a corresponding increase in mass.

Figure 20:
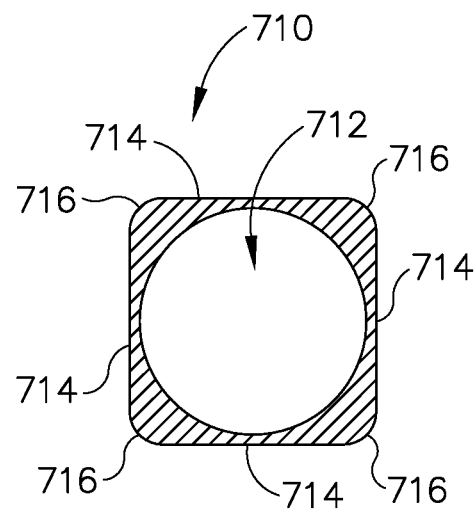
FIG. 20 depicts a cross-sectional view of another exemplary alternative ultrasonic blade.
Figure 21:
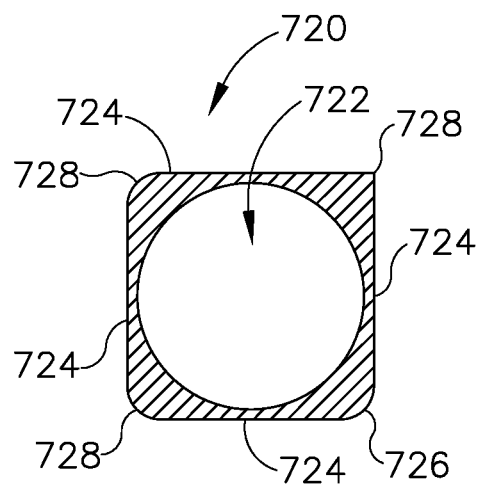
FIG. 21 depicts a cross-sectional view of another exemplary alternative ultrasonic blade.

Sharp corners (706) of ultrasonic blade (700) may provide additional functionality that enhances the ability of ultrasonic blade (700) to be used to perform back scoring and other scalpel-like operations. In the context of a liver procedure, back scoring may be used to cut the Glisson capsule. As an alternative, an ultrasonic blade (710) like the one shown in FIG. 20 may be used. Ultrasonic blade (710) of this example is like ultrasonic blade (700) in that ultrasonic blade (710) includes a lumen (712) with four flat faces (714). However, in this example, faces (714) are joined by corners (716) that are rounded. As another variation, an ultrasonic blade (720) like the one shown in FIG. 21 may be used. Ultrasonic blade (720) of this example is like ultrasonic blade (700) in that ultrasonic blade (720) includes a lumen (722) with four flat faces (724). Ultrasonic blade (720) is like ultrasonic blade (710) in that ultrasonic blade (720) has three rounded corners (726). However, ultrasonic blade (720) further includes one sharp corner (728). Thus, sharp corner (728) may be used to perform back scoring and other scalpel-like operations.

In addition to providing faster tissue fragmentation during the emulsification process (e.g., using blade (700, 710, 720) to transect a liver parenchyma) due to the relatively large cross-sectional area and mass of blades (700, 710, 720), flat faces (704, 714, 724) may provide a better clamping surface to cooperate with clamp pad (76) during the process of transecting and sealing anatomical structures (e.g., when transecting and sealing vessels and biliary ducts of the liver after transection of the liver parenchyma). By providing a better clamping surface to cooperate with clamp pad (76), blade (700, 710, 720) may provide a better seal of transected tissue.

E. Exemplary Ultrasonic Surgical Instrument with Pinching Valve Assembly

Figure 22B:
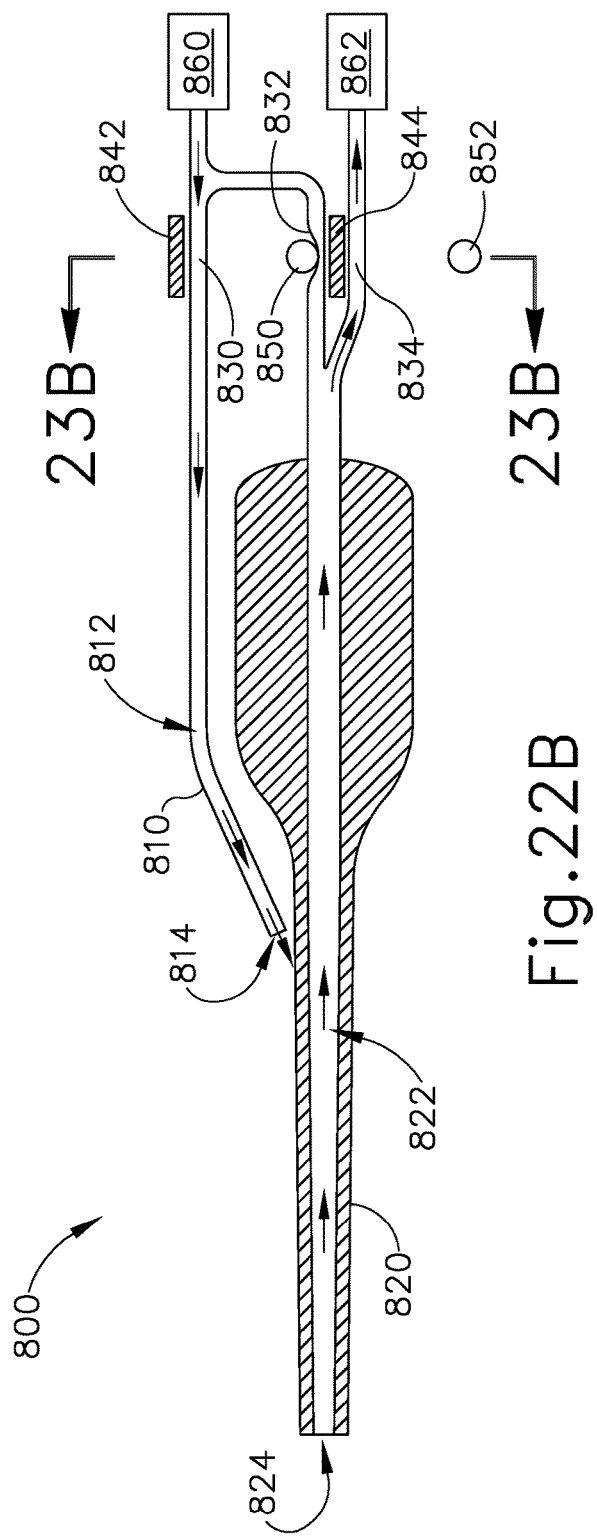
FIG. 22B depicts a cross-sectional side view of the instrument of FIG. 22A, with the valve assembly in a second state.

FIGS. 22A-22C show another exemplary alternative ultrasonic surgical instrument (800). Except as otherwise described below, instrument (800) of this example is configured and operable just like instrument (10) described above. Instrument (800) of this example comprises an irrigation flue (810) and an ultrasonic blade (820). Irrigation flue (810) defines a lumen (812) that distally terminates in a distal opening (814). Lumen (812) is coupled with a fluid communication line (830). Ultrasonic blade (820) defines a lumen (822) that distally terminates in a distal opening (824). Lumen (822) is coupled with a fluid communication line (832) and a suction line (834).

Fluid communication lines (830, 832) are further in communication with a fluid source (860). By way of example only, fluid source (860) may comprise a source of saline. In some versions, the saline is pressurized. In some other versions, the saline is simply gravity-fed. Suction line (834) is in communication with a suction source (862), such as a conventional vacuum pump. Each line (830, 832, 834) comprises a flexible tube in the present example.

Figure 23B:
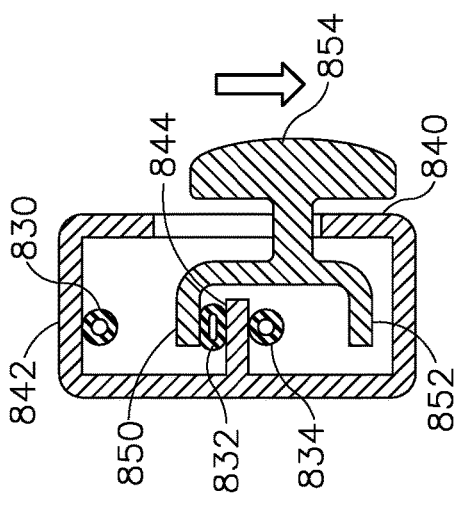
FIG. 23B depicts a cross-sectional view of the valve assembly of the instrument of FIG. 22B, taken along like 23B-23B of FIG. 22B, with the valve assembly in the second state.

As best seen in FIGS. 23A-23C, a valve housing (840) surrounds a portion of each line (830, 832, 834). A translating actuator (854) is slidably coupled with valve housing (840) to form a valve assembly. Actuator (854) includes a first pinch prong (850) and a second pinch prong (852). Fluid communication line (830) is interposed between first pinch prong (850) and an upper pinch wall (842) of housing (840). Fluid communication line (832) is interposed between first pinch prong (850) and an intermediate pinch wall (844) of housing (840). Suction line (834) is interposed between second pinch prong (852) and intermediate pinch wall (844).

Actuator (854) is configured to translate vertically relative to housing (840) to selectively pinch lines (830, 832, 834) against corresponding pinch walls (842, 844) of housing (840). As shown in FIGS. 22A and 23A, actuator (854) may be in a first state where pinch prongs (852) are not pinching any of pinch lines (830, 832, 834). In this state, fluid may flow freely through fluid communication lines (830, 832); and suction may flow freely through suction communication line (834). In some versions, this state is never used during normal operation of instrument (800).

FIGS. 22B and 23B show instrument (800) in a state where actuator (854) is in a downward position. In this state, pinch prong (850) is pinching fluid communication line (832) against intermediate pinch wall (844). This pinching deforms fluid communication line (832) to the point where fluid communication line (832) is effectively sealed, such that fluid from fluid source (860) does not reach lumen (822) of ultrasonic blade (820). However, fluid from fluid source (860) is freely communicated to lumen (812) of irrigation flue (810) via fluid communication lune (830); and suction from suction source (862) is freely communicated to lumen (822) of ultrasonic blade (820) via suction communication line (834). This state may be used during normal operation of instrument (800) to emulsify tissue (e.g., during transection of the parenchyma of a liver).

FIGS. 22C and 23C show instrument (800) in a state where actuator (854) is in an upward position. In this state, pinch prong (850) is pinching fluid communication line (830) against upper inch wall (842); while pinch prong (852) is pinching suction communication line (834) against intermediate pinch wall (834). This pinching deforms lines (830, 834) to the point where lines (830, 834) are effectively sealed. Thus, fluid from fluid source (860) does not reach lumen (812) of irrigation flue (810); and suction from suction source (862) does not reach lumen (822) of ultrasonic blade (820). However, fluid from fluid source (860) is freely communicated to lumen (822) of ultrasonic blade (820) via fluid communication line (832). This state may be used when the operator wishes to clear a clog or other restriction from lumen (822) of ultrasonic blade (820), as the fluid from fluid source (860) may flush debris from lumen (822). Before actuating this state, the operator may re-orient instrument (800) such that distal end (824) of ultrasonic blade (820) is pointed to a waste bin, thereby ensuring that the flushed debris is deposited in the waste bin rather than being deposited at the surgical site.

In the present example, actuator (854) is manually operated. Actuator (854) and housing (840) may include complementary detenting features that selectively retain actuator in the position shown in FIGS. 22B and 23B or the position shown in FIGS. 22C and 23C. Alternatively, actuator (854) and housing (840) may include complementary latching or locking features that selectively retain actuator in the position shown in FIGS. 22B and 23B or the position shown in FIGS. 22C and 23C. As another merely illustrative example, actuator (854) may be replaced with a motor-driven, solenoid-driven, or otherwise non-manually powered feature to selectively transition between the state shown in FIGS. 22B and 23B and the state shown in FIGS. 22C and 23C. In some such versions, a controller may automate the transition between states. For instance, a combination like that shown in FIG. 10 may execute a method like method (450) of FIG. 11 to automate the selective transitioning between the state shown in FIGS. 22B and 23B and the state shown in FIGS. 22C and 23C.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument, comprising: (a) an ultrasonic blade, wherein the ultrasonic blade defines a distal opening, wherein the ultrasonic blade is operable in a first mode to emulsify tissue that is distally positioned relative to the ultrasonic blade, wherein the ultrasonic blade is further operable in a second mode to transect and seal tissue that is transversely positioned relative to the ultrasonic blade; (b) a first fluid port in communication with the distal opening of the ultrasonic blade; (c) an irrigation member positioned adjacent to the distal end of the ultrasonic blade; (d) a second fluid port in communication with the irrigation member; and (e) a fluid communication assembly, wherein the fluid communication assembly is configured to: (i) couple the first fluid port with a fluid source, (ii) couple the first fluid port with a suction source, and (iii) couple the second fluid port with the fluid source.

Example 2

The instrument of Example 1, further comprising a clamp arm, wherein the clamp arm is pivotable toward and away from the ultrasonic blade to cooperate with the ultrasonic blade in the second mode.

Example 3

The instrument of any one or more of Examples 1 through 2, wherein the fluid communication assembly further comprises a controller, wherein the controller is configured to execute a control algorithm that includes alternating between coupling the first fluid port with the fluid source for a first duration and coupling the first fluid port with the suction source for a second duration.

Example 4

The instrument of Example 3, wherein the first duration is longer than the second duration.

Example 5

The instrument of Example 3, wherein the first duration is shorter than the second duration.

Example 6

The instrument of any one or more of Examples 3 through 5, wherein the fluid communication assembly further comprises a sensor, wherein the sensor is operable to detect a clog or other restriction in the ultrasonic blade, wherein the sensor is in communication with the controller.

Example 7

The instrument of Example 6, wherein the controller is configured to provide a first duty cycle in response to the sensor failing to detect a clog or other restriction in the ultrasonic blade, wherein the first duration is shorter than the second duration during the first duty cycle.

Example 8

The instrument of Example 7, wherein the controller is configured to provide a second duty cycle in response to the sensor detecting a clog or other restriction in the ultrasonic blade, wherein the first duration is longer than the second duration during the second duty cycle.

Example 9

The instrument of any one or more of Examples 1 through 8, wherein the ultrasonic blade further defines a distal lumen portion and a proximal lumen portion, wherein the lumen portions are in fluid communication with the distal opening, wherein the lumen portions are coaxially aligned with each other, wherein the proximal lumen portion has a larger diameter than the distal lumen portion.

Example 10

The instrument of Example 9, wherein the ultrasonic blade further defines a tapered inner sidewall, wherein the tapered inner sidewall provides a tapered transition from the distal lumen portion to the proximal lumen portion.

Example 11

The instrument of any one or more of Examples 1 through 10, further comprising a shaft surrounding a portion of the ultrasonic blade, wherein the shaft includes a movable hatch, wherein the hatch is movable to selectively uncover a portion of the ultrasonic blade.

Example 12

The instrument of Example 11, wherein the ultrasonic blade defines a lumen and a lateral opening, wherein the lumen is in fluid communication with the distal opening, wherein the lateral opening is in fluid communication with the lumen, wherein the lateral opening is spaced proximally from the distal opening.

Example 13

The instrument of Example 12, wherein the hatch is positioned to selectively cover and uncover the lateral opening.

Example 14

The instrument of Example 13, wherein the hatch comprises a gasket, wherein the gasket is configured to seal the lateral opening when the hatch is in a closed position, wherein the gasket is configured to open the lateral opening when the hatch is in an open position.

Example 15

The instrument of any one or more of Examples 1 through 14, wherein the ultrasonic blade has a generally square shaped cross-sectional profile.

Example 16

The instrument of Example 15, wherein the generally square shaped cross-sectional profile includes at least one rounded corner.

Example 17

The instrument of Example 16, wherein the generally square shaped cross-sectional profile includes at least one sharp corner.

Example 18

The instrument of any one or more of Examples 1 through 17, wherein the fluid communication assembly further comprises: (i) a set of flexible conduits, (ii) a set of pinching members, and (iii) a set of pinching surfaces, wherein the pinging members are operable to selectively pinch the flexible conduits against the pinching surfaces to thereby selectively control fluid flow between: (A) the first fluid port and the fluid source, (B) the first fluid port and the suction source, and (C) the second fluid port and the fluid source.

Example 19

An instrument, comprising: (a) an ultrasonic blade, wherein the ultrasonic blade comprises: (i) an elongate shaft, (ii) a lumen extending through the elongate shaft, (iii) distal opening located at a distal end of the shaft, wherein the distal opening is in fluid communication with the lumen, (iv) a lateral opening spaced proximally apart from the distal end, wherein the lateral opening is in fluid communication with the lumen; (b) a body including an elongate outer shaft, wherein the elongate outer shaft defines a lateral opening corresponding with the lateral opening of the ultrasonic blade; and (c) a hatch movably coupled with the elongate outer shaft at the lateral opening of the elongate outer shaft, wherein the hatch includes an inner gasket, wherein the gasket is configured to selectively seal the lateral opening of the ultrasonic blade.

Example 20

A method of operating an instrument, the method comprising: (a) expelling fluid at a surgical site through an irrigation member, wherein the irrigation member is positioned adjacent to an ultrasonic blade; (b) applying ultrasonic energy at the surgical site via the ultrasonic blade; and (c) alternating between: (i) applying suction through a lumen of the ultrasonic blade at the surgical site, and (ii) expelling fluid through the lumen of the ultrasonic blade at the surgical site.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
 (a) an ultrasonic blade, wherein the ultrasonic blade defines a distal opening, wherein the ultrasonic blade is operable to transect and seal tissue that is transversely positioned relative to the ultrasonic blade, wherein the ultrasonic blade further defines a distal lumen portion and a proximal lumen portion, wherein the distal and proximal lumen portions are coaxially aligned and in fluid communication with the distal opening, wherein the proximal lumen portion has a larger inner diameter than the distal lumen portion;

(b) a first fluid port in fluid communication with the distal opening of the ultrasonic blade;

(c) an irrigation member having an irrigation opening positioned adjacent to a distal end of the ultrasonic blade;

(d) a second fluid port in fluid communication with the irrigation opening of the irrigation member; and (e) a fluid communication assembly fluidly connected to the first and second fluid ports and having a fluid inlet port and a suction inlet port respectively configured to connect to a fluid source and a suction source, wherein the fluid communication assembly is configured to:
(i) couple the first fluid port with the fluid inlet port for distally directing a fluid from the fluid source from the first fluid port toward the distal opening,
(ii) couple the first fluid port with the suction inlet port for proximally directing a suction to the suction source from the distal opening toward the first fluid port, and
(iii) couple the second fluid port with the fluid inlet port for distally directing the fluid from the fluid source from the second fluid port toward the irrigation opening,
wherein the ultrasonic blade further defines a lateral opening and the proximal and distal lumen portions define a lumen, wherein the lateral opening is in fluid communication with the lumen and the distal opening, and wherein the lateral opening is spaced proximally from the distal opening, and further comprising a shaft surrounding a portion of the ultrasonic blade, wherein the shaft includes a movable hatch, wherein the hatch is movable to selectively uncover a portion of the ultrasonic blade.

2. The ultrasonic surgical instrument of claim 1, further comprising a clamp arm, wherein the clamp arm is pivotable toward and away from the ultrasonic blade to cooperate with the ultrasonic blade.

3. The ultrasonic surgical instrument of claim 1, wherein the fluid communication assembly further comprises a controller, wherein the controller is configured to execute a control algorithm that includes alternating between coupling the first fluid port with the fluid inlet port for a first duration and coupling the first fluid port with the suction inlet port for a second duration.

4. The ultrasonic surgical instrument of claim 3, wherein the first duration is longer than the second duration.

5. The ultrasonic surgical instrument of claim 3, wherein the first duration is shorter than the second duration.

6. The ultrasonic surgical instrument of claim 3, wherein the fluid communication assembly further comprises a sensor, wherein the sensor is operable to detect a clog, wherein the sensor is in communication with the controller.

7. The ultrasonic surgical instrument of claim 6, wherein the controller is configured to provide a first duty cycle in response to the sensor failing to detect the clog, wherein the first duration is shorter than the second duration during the first duty cycle.

8. The ultrasonic surgical instrument of claim 7, wherein the controller is configured to provide a second duty cycle in response to the sensor detecting the clog, wherein the first duration is longer than the second duration during the second duty cycle.

9. The ultrasonic surgical instrument of claim 1, wherein the ultrasonic blade further defines a tapered inner sidewall within the ultrasonic blade, wherein the tapered inner sidewall provides a tapered transition from the distal lumen portion defined within the ultrasonic blade to the proximal lumen portion defined within the ultrasonic blade.

10. The ultrasonic surgical instrument of claim 1, wherein the hatch is positioned to selectively cover and uncover the lateral opening.

11. The ultrasonic surgical instrument of claim 1, wherein the ultrasonic blade has a generally square shaped cross-sectional profile.

12. The ultrasonic surgical instrument of claim 1, wherein the fluid communication assembly further comprises:
(i) a set of flexible conduits,
(ii) a set of pinching members, and
(iii) a set of pinching surfaces,
wherein the pinching members are operable to selectively pinch the flexible conduits against the pinching surfaces to thereby selectively control fluid flow between:
(A) the first fluid port and the fluid source,
(B) the first fluid port and the suction source, and
(C) the second fluid port and the fluid source.

13. The ultrasonic surgical instrument of claim 12, wherein the irrigation member at least partially defines a fluid lumen extending distally to the irrigation opening, wherein the fluid lumen is fluidly connected to the second fluid port and offset apart from the ultrasonic blade.

14. The ultrasonic surgical instrument of claim 13, further comprising a clamp arm movably secured relative to the ultrasonic blade from an open position away from the ultrasonic blade toward a closed position adjacent to the ultrasonic blade to cooperate with the ultrasonic blade, wherein the ultrasonic blade extends along a longitudinal axis in a longitudinal direction.

15. The ultrasonic surgical instrument of claim 1, wherein the distal and proximal lumen portions are coaxially aligned with the distal opening.

16. An ultrasonic surgical instrument, comprising:
(a) an ultrasonic blade, wherein the ultrasonic blade defines a distal opening, wherein the ultrasonic blade is operable to transect and seal tissue that is transversely positioned relative to the ultrasonic blade;
(b) a first fluid port in fluid communication with the distal opening of the ultrasonic blade;
(c) an irrigation member positioned proximate to the ultrasonic blade and at least partially defining a fluid lumen distally extending to an irrigation opening positioned adjacent to a distal end of the ultrasonic blade, wherein the fluid lumen is offset apart from the ultrasonic blade;
(d) a second fluid port in fluid communication with the irrigation opening of the irrigation member via the fluid lumen extending therebetween;
(e) a fluid communication assembly, wherein the fluid communication assembly is configured to:
(i) couple the first fluid port with a fluid source,
(ii) couple the first fluid port with a suction source, and
(iii) couple the second fluid port with the fluid source; and
(f) a hatch covering a portion of the ultrasonic blade, wherein the hatch is movable relative to the ultrasonic blade to selectively uncover the portion of the ultrasonic blade.

17. The ultrasonic surgical instrument of claim 16, further comprising a shaft surrounding at least a portion of the ultrasonic blade, and wherein the shaft includes the hatch.

18. The ultrasonic surgical instrument of claim 16, wherein the ultrasonic blade defines a lumen and a lateral opening, wherein the lumen is in fluid communication with the distal opening, wherein the lateral opening is in fluid communication with the lumen, wherein the lateral opening is spaced proximally from the distal opening, and wherein the hatch is positioned to selectively cover and uncover the lateral opening.

19. An ultrasonic surgical instrument, comprising:
(a) an ultrasonic blade, wherein the ultrasonic blade defines a distal opening, wherein the ultrasonic blade is operable to transect and seal tissue that is transversely positioned relative to the ultrasonic blade;
(b) a first fluid port in fluid communication with the distal opening of the ultrasonic blade;
(c) an irrigation member positioned proximate to the ultrasonic blade and at least partially defining a fluid lumen distally extending to an irrigation opening positioned adjacent to a distal end of the ultrasonic blade, wherein the fluid lumen is offset apart from the ultrasonic blade;
(d) a second fluid port in fluid communication with the irrigation opening of the irrigation member via the fluid lumen extending therebetween; and
(e) a fluid communication assembly configured to configured to couple the first fluid port with a fluid source, couple the first fluid port with a suction source, and couple the second fluid port with the fluid source, wherein the fluid assembly includes:
  (i) a plurality of flexible conduits,
  (ii) a plurality of pinching members, and
  (iii) a plurality of pinching surfaces,
  wherein the plurality of pinching members are operable to selectively pinch the plurality of flexible conduits against the plurality of pinching surfaces to thereby selectively control fluid flow between the first fluid port and the fluid source, the first fluid port and the suction source, and the second fluid port and the fluid source.

* * * * *